(12) United States Patent
Vachula et al.

(10) Patent No.: US 6,458,585 B1
(45) Date of Patent: Oct. 1, 2002

(54) CYTOKINE-FREE CULTURE OF DENDRITIC CELLS

(75) Inventors: Mona Vachula, Lake Villa, IL (US); Dennis E. Van Epps, Coto de Caza, CA (US); Mortimer T. Alzona, Vernon Hills; Frederick M. Aono, Arlington Hills, both of IL (US)

(73) Assignee: Nexell Therapeutics Inc., Irvine, CA (US)

( * ) Notice: Subject to any disclaimer, the term of this patent is extended or adjusted under 35 U.S.C. 154(b) by 0 days.

(21) Appl. No.: 08/904,124

(22) Filed: Jul. 31, 1997

Related U.S. Application Data

(63) Continuation-in-part of application No. 08/840,213, filed on Apr. 11, 1997, which is a continuation-in-part of application No. 08/696,747, filed on Aug. 14, 1996, now abandoned.

(51) Int. Cl.$^7$ ................................................. C12N 5/00
(52) U.S. Cl. ................. 435/325; 435/366; 435/363; 435/372; 435/405; 435/347
(58) Field of Search ................. 435/347, 363, 435/366, 372, 405, 325

(56) References Cited

U.S. PATENT DOCUMENTS

| | | | |
|---|---|---|---|
| 5,399,493 A | 3/1995 | Emerson et al. | 435/172.3 |
| 5,437,994 A | 8/1995 | Emerson et al. | 435/240.2 |
| 5,605,822 A | 2/1997 | Emerson et al. | 435/172.3 |
| 5,646,043 A | 7/1997 | Emerson et al. | 435/373 |
| 5,670,147 A | 9/1997 | Emerson et al. | 424/93.1 |
| 5,670,351 A | 9/1997 | Emerson et al. | 435/172.3 |
| 5,849,589 A | 12/1998 | Tedder et al. | 435/377 |
| 5,851,756 A | 12/1998 | Steinman et al. | 435/2 |
| 5,866,115 A | 2/1999 | Kanz et al. | 424/93.7 |
| 5,871,728 A | 2/1999 | Thomson et al. | 424/93.7 |
| 5,994,126 A | 11/1999 | Steinman et al. | 435/325 |
| 6,004,807 A | 12/1999 | Banchereau et al. | 435/325 |
| 6,010,905 A | 1/2000 | Cohen et al. | 435/372 |
| 6,017,527 A | 1/2000 | Maraskovsky et al. | 424/93.71 |

FOREIGN PATENT DOCUMENTS

| | | |
|---|---|---|
| WO | WO 93/20185 | 10/1993 |

OTHER PUBLICATIONS

Mayani et al., Experimetnal Hematology, 23:422–427, 1995.*
Jaffe, Pediatric Pathology, 13:821–837, 1993.*
Lardon et al., Experimental Hematology, 22:903–908, 1994.*
Snoeck et al., J. Exp. Med., 183:705–710, 1996.*
Thomas et al., Stem cells, 14:196–206, 1996.*
Williams et al., International Review of Cytology, 153:41–103, 1994.*

* cited by examiner

*Primary Examiner*—Leon B. Lankford, Jr.
(74) *Attorney, Agent, or Firm*—Campbell & Flores LLP

(57) ABSTRACT

A method for producing human dendritic cells for therapeutic purposes which allows culture-deriving dendritic cells using no cytokines, or reduced cytokines. The method involves culturing mononuclear cells from blood or bone marrow in a medium containing at least one agent such as a calcium ionophore, e.g. A23187, theophylline, protaglandin E1, dibutyryl cyclic AMP, Vitamin D3, Vitamin E, retinoic acid, or a fatty acid. The culture is maintained for a sufficient time, typically 4–14 days, to produce a culture enriched for dendritic cells, as evidenced by at least about 2.5% of total cells exhibiting dendritic cell processes, or a dendritic dell antigen such as CD80, CD86, or CD1a. Also provided is a method to produce antigen-specific human T-cells by pulsing the dendritic cells obtained by the method of the invention with an antigen such as a viral, tumor, bacterial, or cell surface antigen, and then co-culturing T-cells with the antigen-pulsed dendritic cells. Useful for treatment of viral or bacterial infections, useful as a cancer vaccine, useful to induce tolerance of allo- or xeno- graft.

36 Claims, 9 Drawing Sheets

CYTOKINE-FREE CULTURE OF DENDRITIC CELLS

REFERENCE TO RELATED APPLICATIONS

This is a continuation-in-part of U.S. application Ser. No. 08/840,213, filed Apr. 11, 1997, which is a continuation-in-part of U.S. Ser. No. 08/696,747, filed Aug. 14, 1996 now abandoned.

TECHNICAL FIELD

This invention is in the field of ex vivo culture of hematopoietic cells, more specifically in the culture of human dendritic cells and T-cells for therapeutic purposes.

BACKGROUND

Dendritic cells play an important role in immune responses. They provide the immune system with an effective means of antigen presentation, unlike that of any other cell. Dendritic cells are the most potent antigen presenting cells in the immune system. They have been characterized to have a unique morphology and cell surface phenotype that may contribute to their potency in initiating cellular immune responses, specifically T cell dependent responses. Therefore, dendritic cells have been proposed as a valuable component in cellular based therapies that require presentation of antigen to effector cells. Dendritic effector cells can be primed ex vivo to create activated cells to be reintroduced into the body in order to combat disease. However, dendritic cells comprise less than 1% of leukocytes circulating in peripheral blood, which makes it difficult to obtain an amount sufficient to use in therapy.

Dendritic Cells (DC) along with monocytes/macrophages and B lymphocytes are considered professional antigen-presenting cells (APC); (reviews by Caux et al., *Immunology Today* 16: 2–4, 1995; Steinman, *Annu. Rev. Immunol* 9: 271–296, 1991; Young, J W, et al., *Stem Cells* 14:376–387, 1996; Steinman, R M, *Exptl Hematol* 24:859–882, 1996). Even though antigen-presenting cells take in, process, and present antigen to T lymphocytes, they serve different immune functions. DC are the most potent initiators of the immune response and are the APCs responsible for the induction of primary antigen-specific immune reactions (Bhardwaj et al., *J. Exp. Med.* 175: 267–273, 1992; Bhardwaj et al., *J. Exp. Med.* 178: 633–642, 1993). The DC, as are all hematopoietic cells, are derived from CD34+ stem cells. These hematopoietic cells arise in the bone marrow and as they mature traffic to the peripheral blood where they circulate (T cells make a detour to the thymus) and then may enter tissues. The differentiation pathway from a CD34+ cell to a DC is not completely understood (Santiago-Schwarz et al., *J. Leukoc. Biol.* 52: 274–281, 1992; Galy et al., *Immunity* 3: 459–473, 1995; Rosenzwajg et al., *Blood* 87: 535–544, 1996). DC are found in very low levels in peripheral blood (<1%) compared to other white blood cells (WBC) or leukocytes (neutrophils about 60%, lymphocytes about 35%, monocytes about 5%, eosinophils about 2%, basophils <1%); (*Laboratory Medicine Hematology*, editor: J. Miale, publisher: C.V. Mosby Co., 1982). Thus, in order to use DC therapeutically, it would be most practical to expand them ex vivo. To date, the culture of DC cells has been performed in serum-containing media and semi-closed tissue culture plates or flasks. To expand DC under these conditions, GM-CSF appears to be important for DC differentiation, and addition of TNF-α appears to be inhibitory to other CD34+ progenitors as greater DC are seen in those cultures (Santiago-Schwarz et al., *Blood* 82: 3019–3028, 1993). Addition of IL-4 causes the down regulation of CD14+ monocytes (Sallusto et al., *J. Exp. Med.* 179: 1109–1118, 1994; Romani et al., *J. Exp. Med.* 180: 83–93, 1994). Thus cultures that included those cytokines have shown preferential outgrowth of DC.

To date, DC have been identified by a bundle of criteria that cover different features of DC—morphology, phenotype, and their function in mixed lymphocyte reactions (MLR) have been evaluated (O'Doherty et al., *J. Exp. Med.*, 178: 1067–1078, 1993; Freudenthal and Steinman, *PNAS* 87: 7698–7702, 1990; Crow et al., *Clin. Exp. Immunol.* 49: 338–346, 1982; Caux et al., *J. Exp. Med.* 180: 1841–1847, 1994).

Morphologically, DC are identified by their cytoplasmic processes or "veils" that extend from the surface of the cells. The unusual morphology of DC has been described in many publications and illustrated in photomicrographs. For example, Young and Steinman describe DC thusly: "DC extend long processes, easily 10μ in length, in many directions from the cell body. In the living state, these processes are sheet-like "veils" or lamellipodia and are actively motile. When spun onto glass slides, the DC processes are numerous and spiny". (Young, J W, et al., i Stem Cells 14:376–387, 1996.)

Phenotypically, DC constitutively express CD80 and CD86, the costimulatory molecules that bind CD28 on T cells. The ability to stimulate T-cells in an allogeneic mixed lymphocyte reaction is a functional capacity attributed to DC. It has recently been shown that DC are very efficient presenters of antigen and can result in potent CD8+ cytotoxic T cell responses (Bender et al., *J. Exp. Med.* 182: 1663–1671, 1995; Tjoa et al., *The Prostate* 28: 65–69, 1996).

It has been shown that DC can be culture derived from renal cell carcinoma patients (Radmayr et al., *Int. J. Cancer* 63: 627–632, 1995). When DC are isolated from prostate cancer patients that have undergone various immunocompromising therapies, the DC are functional after being in culture ex vivo (Tjoa et al., *The Prostate* 27: 63–69, 1995).

Ronald Levy's group has reported remissions in B-cell lymphoma patients treated with autologous DC which had been isolated from their peripheral blood (Hsu, F. J., et al, *Nature Medicine* 2:52–57, 1996). The monocyte-depleted leukapheresis product was initially cultured for 24 hours with an idiotype protein surface antigen specific to each patient's tumor; then DC were purified by differential gradient centrifugation, and returned to culture for an additional 14–18 hours prior to intravenous administration of the DC.

DC culture to date has been performed in medium containing cytokines such as granulocyte/macrophage-colony stimulating factor (GM-CSF), interleukin-4 (IL-4), tumor necrosis factor-α (TNF-α), and stem cell factor (SCF). The development of recombinant forms of these cytokines in recent years has made their use in the clinical setting much more practical than it would otherwise have been when they were only available in small quantities purified from natural sources. However, recombinant proteins are expensive, and not always available in a form needed for clinical use, i.e. produced under Good Manufacturing Conditions (GMC). Moreover, clinical trials are required to obtain regulatory approval for the clinical use of each individual cytokine.

There have been reports in the literature of using small molecules in attempts to promote differentiation of hematopoietic cells other than DC. T and B cells were stimulated with L-leucine methyl ester, which caused the death of monocytes (Thiele, et al. 1983 *J Immunol.* 131:2282–2290).

Thiele et al. also reported using mitogens such as plant lectins, concanavalin A, pokeweed, sodium periodate, and neuraminidase plus galactose oxidase. Terminal monocyte differentiation in cell lines was potentiated by the combination of transforming growth factor-β plus Vitamin D3 (Testa, et al. *J Immunol.* 1993 150:2418–2430). Vitamin D2 was reported to increase differentiation of monocytes in a cell line, while retinoic acid did not (Howell, et al. 1994 *Blood Coagulation and Fibrinolysis* 5:445–453). Leukemia cell lines were reported to increase their differentiation to mature granulocytes, or monocytes/macrophages, or erythroid cells upon stimulation with tubulin disruptors, TPA, retinoids, or hemin (Nakajima, et al. 1994 *Biol. Pharm. Bull.* 17:742–744). The HL60 cell line was reported to show increased differentiation towards neutrophils or monocytes upon stimulation with retinoids and Vitamin D3 (Bunce et al. 1995 *Leukemia* 9:410–418).

It would be most advantageous to be able to culture DC without the use of cytokines, or with only one cytokine, using only common molecules which are readily available, inexpensive, and possibly already approved for use in the clinical setting.

SUMMARY OF THE INVENTION

Figure 1:
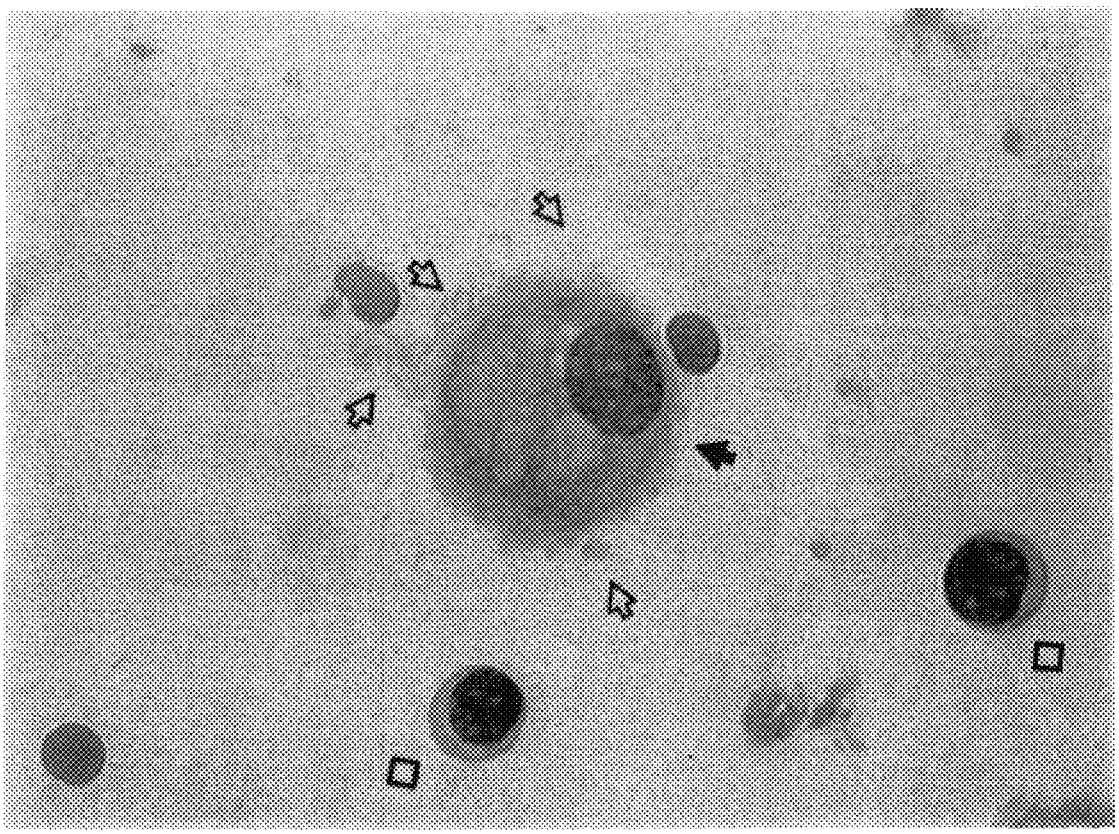
FIG. 1 shows a Wright-Giemsa-stained dendritic cell (DC; solid arrow) produced by the method of the invention. The hollow arrows indicate processes or "veils" typical of DC. The hollow diamonds indicate lymphocytes which remained in the DC culture.
Figure 2:
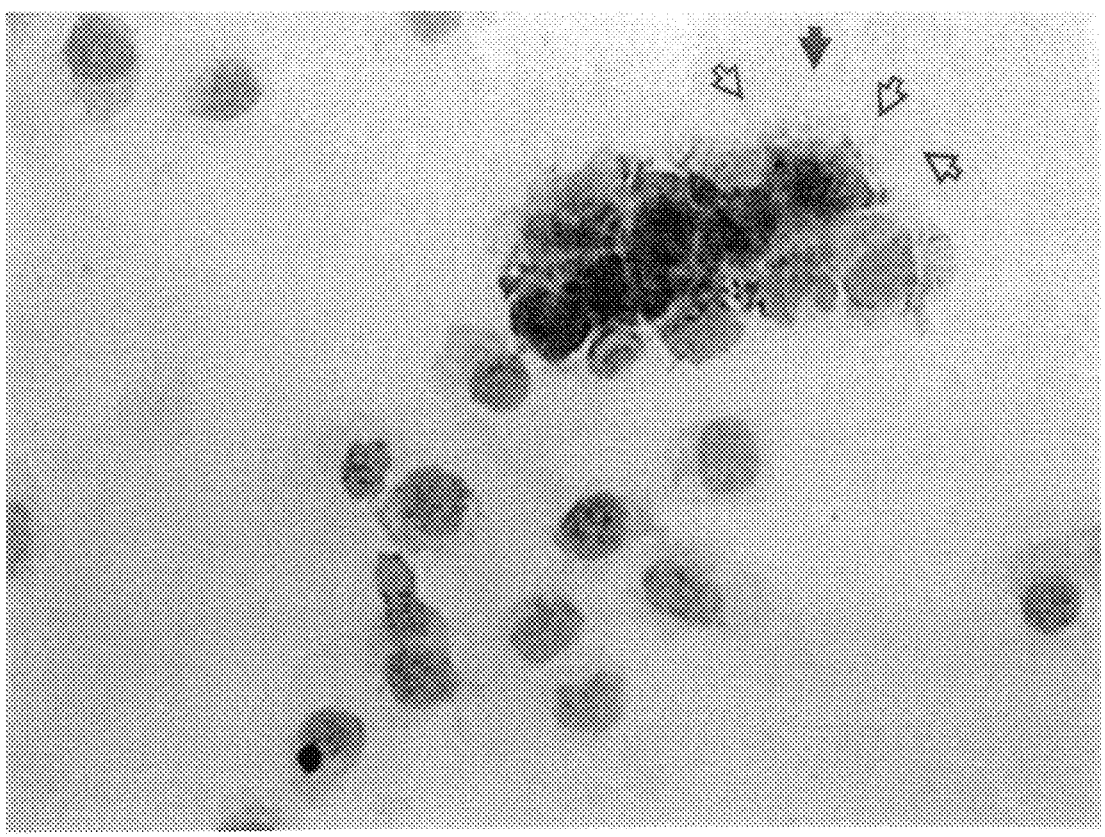
FIG. 2 shows a clump of DC produced by a positive-control method using animal serum (RPMI+10%FCS); the DC are stained with an antibody to CD86. Hollow arrows indicate processes and veils typical of DC.
Figure 3:
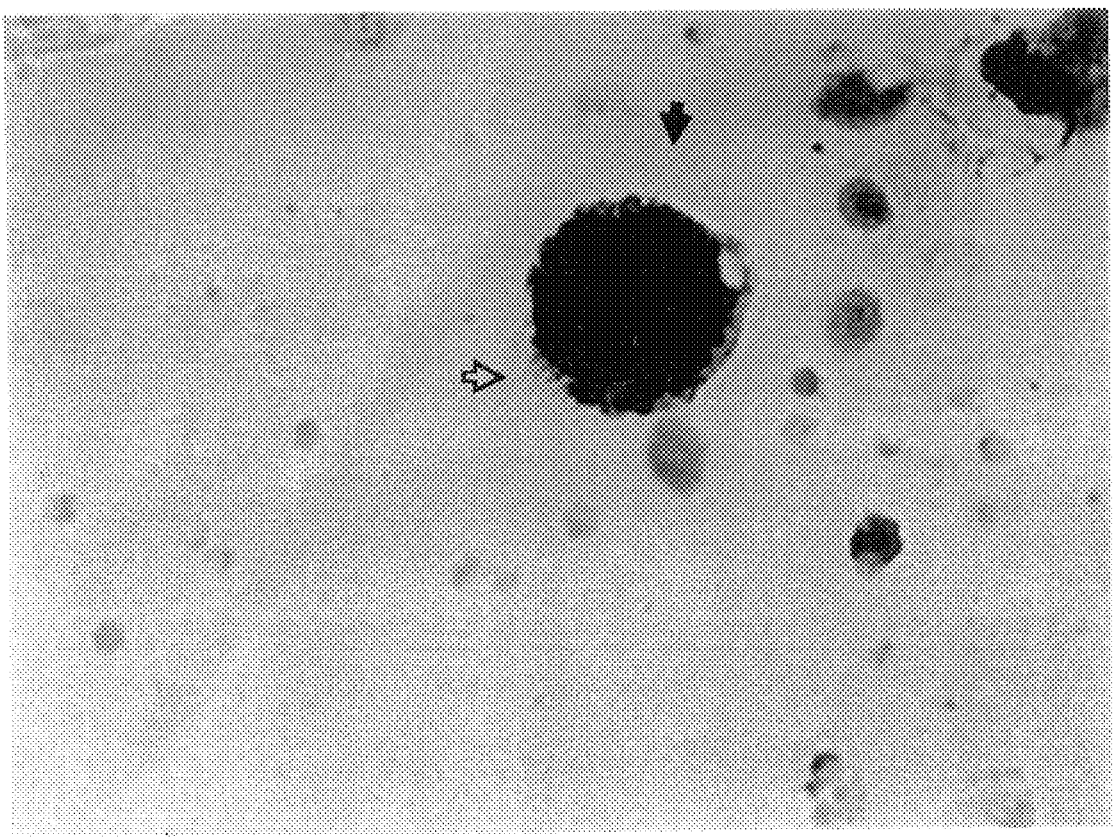
FIG. 3 shows a DC (solid arrow) in a culture produced by the method of the invention and stained with an antibody to CD86. The hollow arrow indicates typical DC processes.
Figure 4:
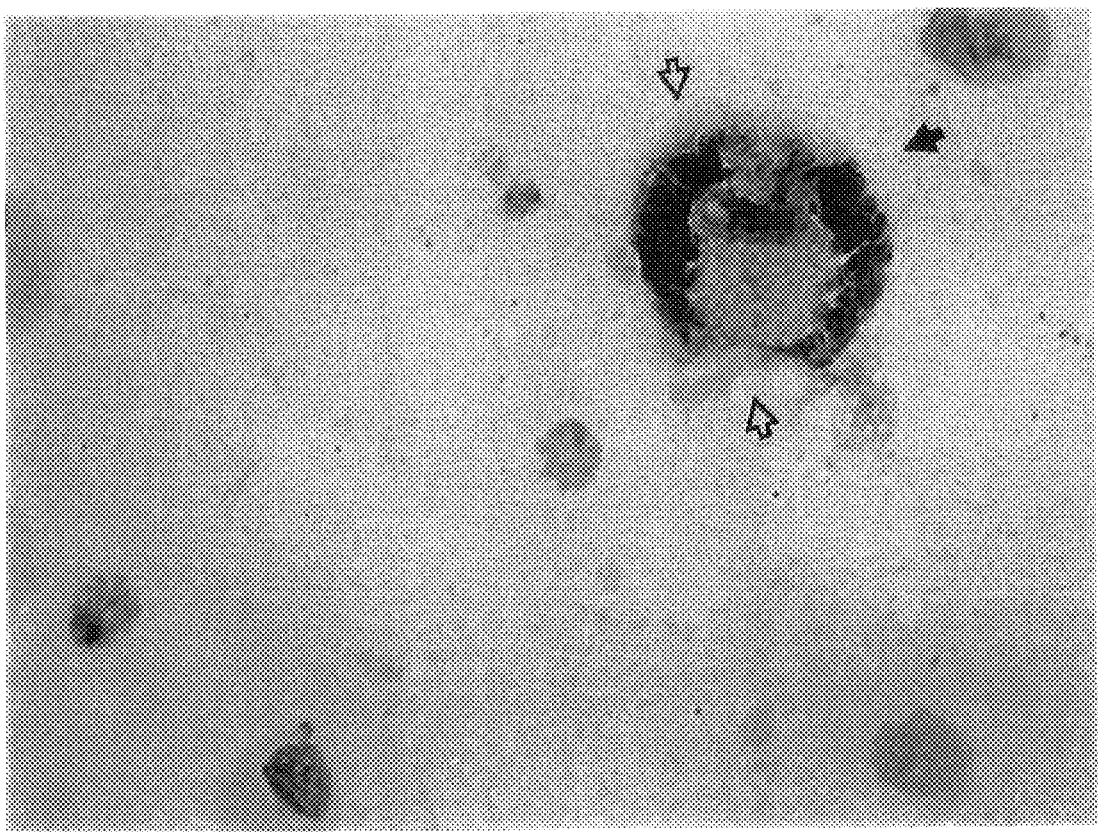
FIG. 4 shows a DC (solid arrow) produced by the method of the invention and stained with an antibody to CD80. The hollow arrows indicate typical DC processes.
Figure 5:
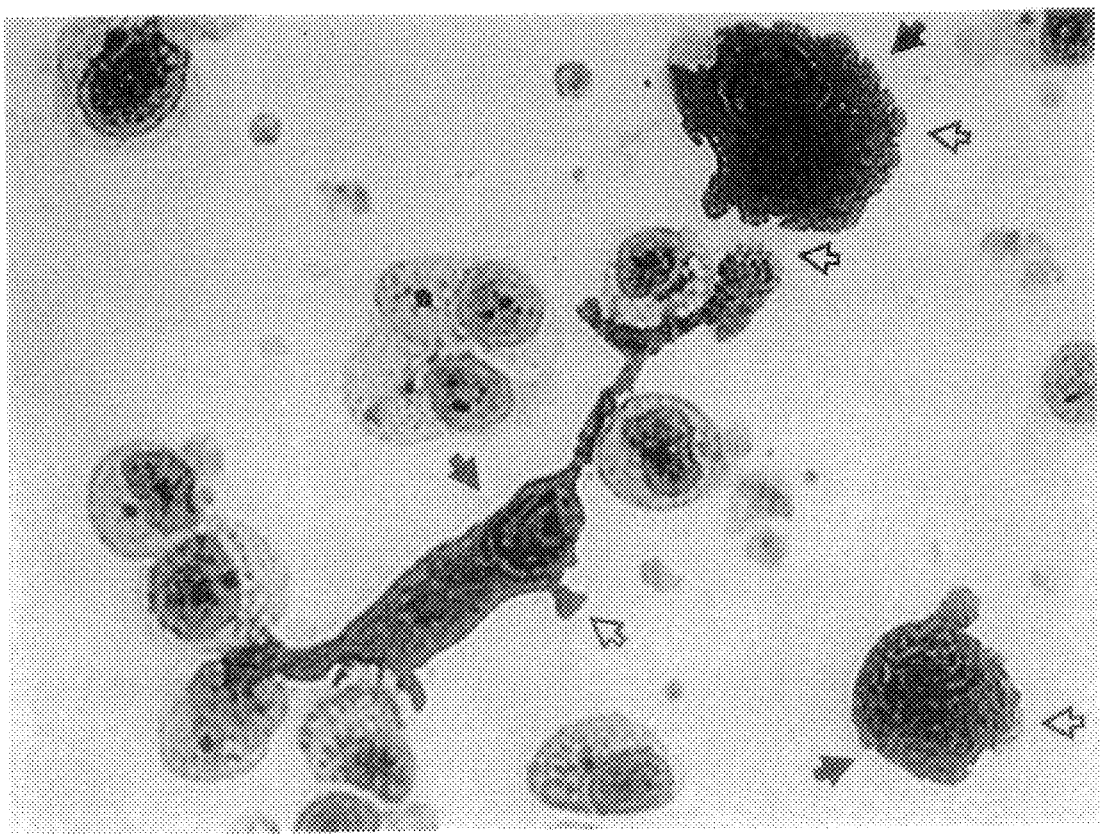
FIG. 5 shows DC (solid arrows) produced by the method of the invention and stained with S100 antibody. Hollow arrows indicate processes typical of DC. This photo suggests how DC may contact and interact with lymphocytes, which in this culture were lymphocytes remaining in the DC culture.
Figure 6:
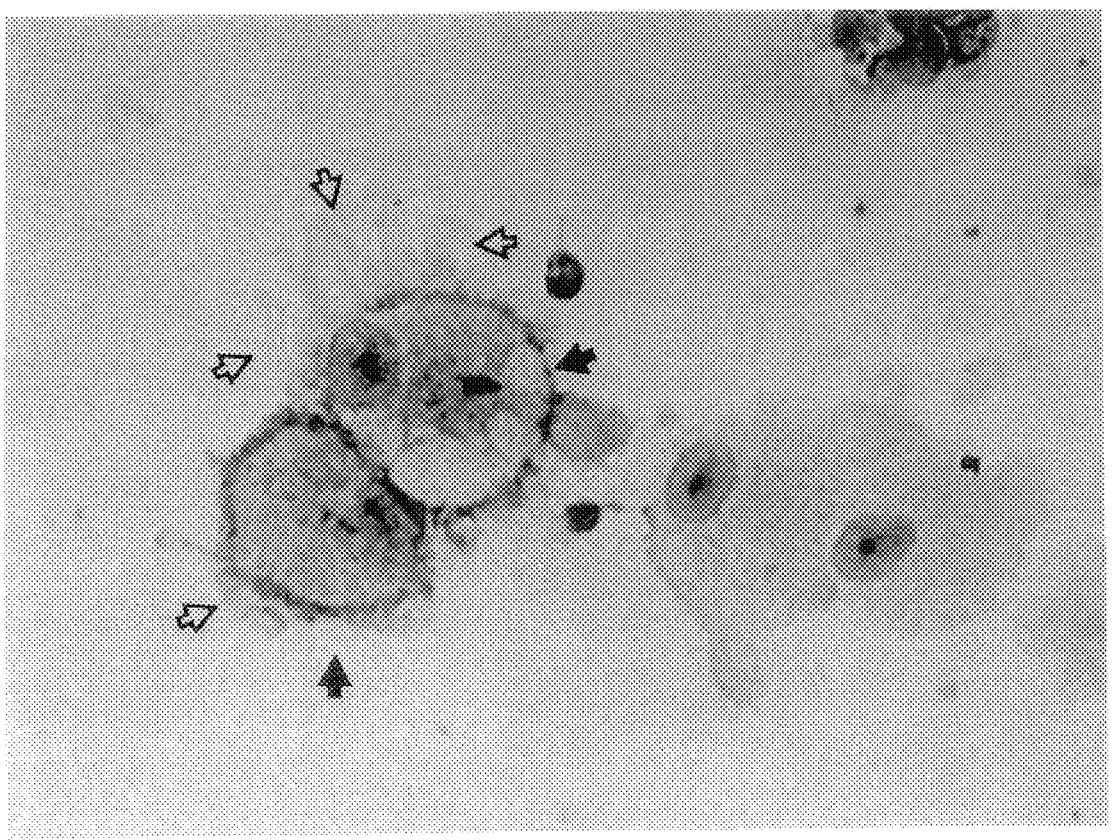
FIG. 6 shows DC (solid arrows) produced from a commercially-available research source, using the commercially-valiable method, as a positive control. The cells are stained with an antibody to CD86. Hollow arrows indicate processes typical of DC.
Figure 7:
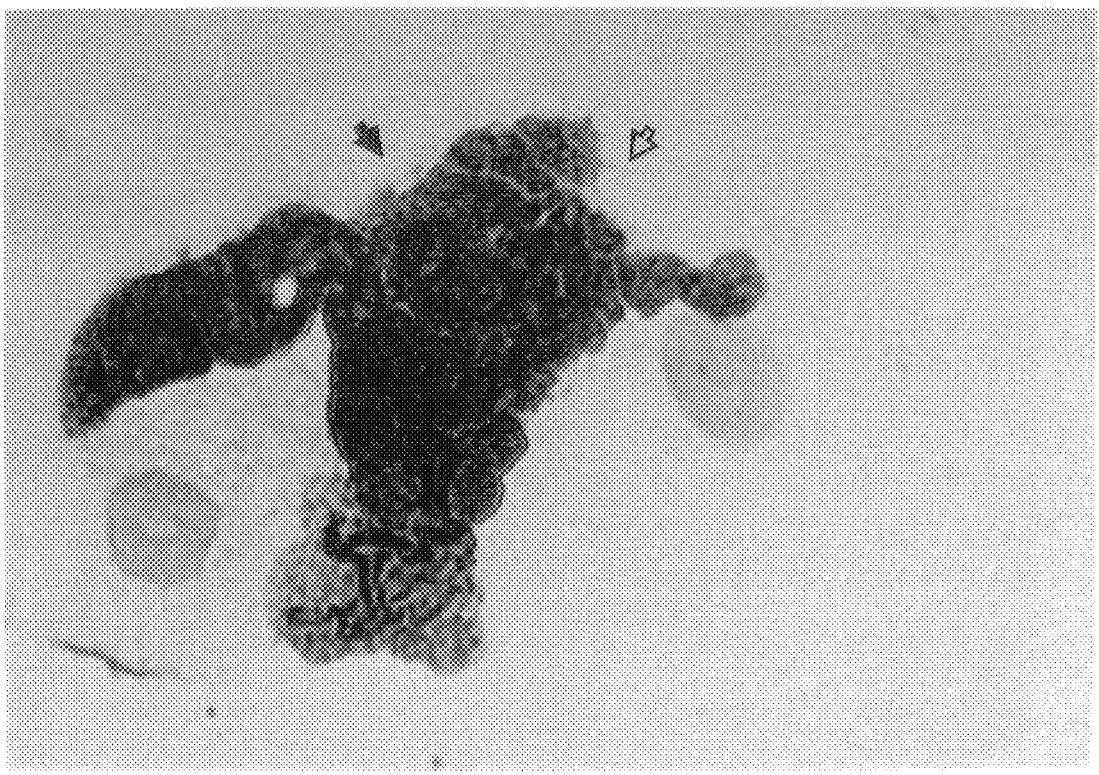
FIG. 7 shows a clump of DC produced from the same commercially-available source as in FIG. 6. The cells are stained with an S100 antibody. The hollow arrow indicates a process typical of DC.
Figure 8:
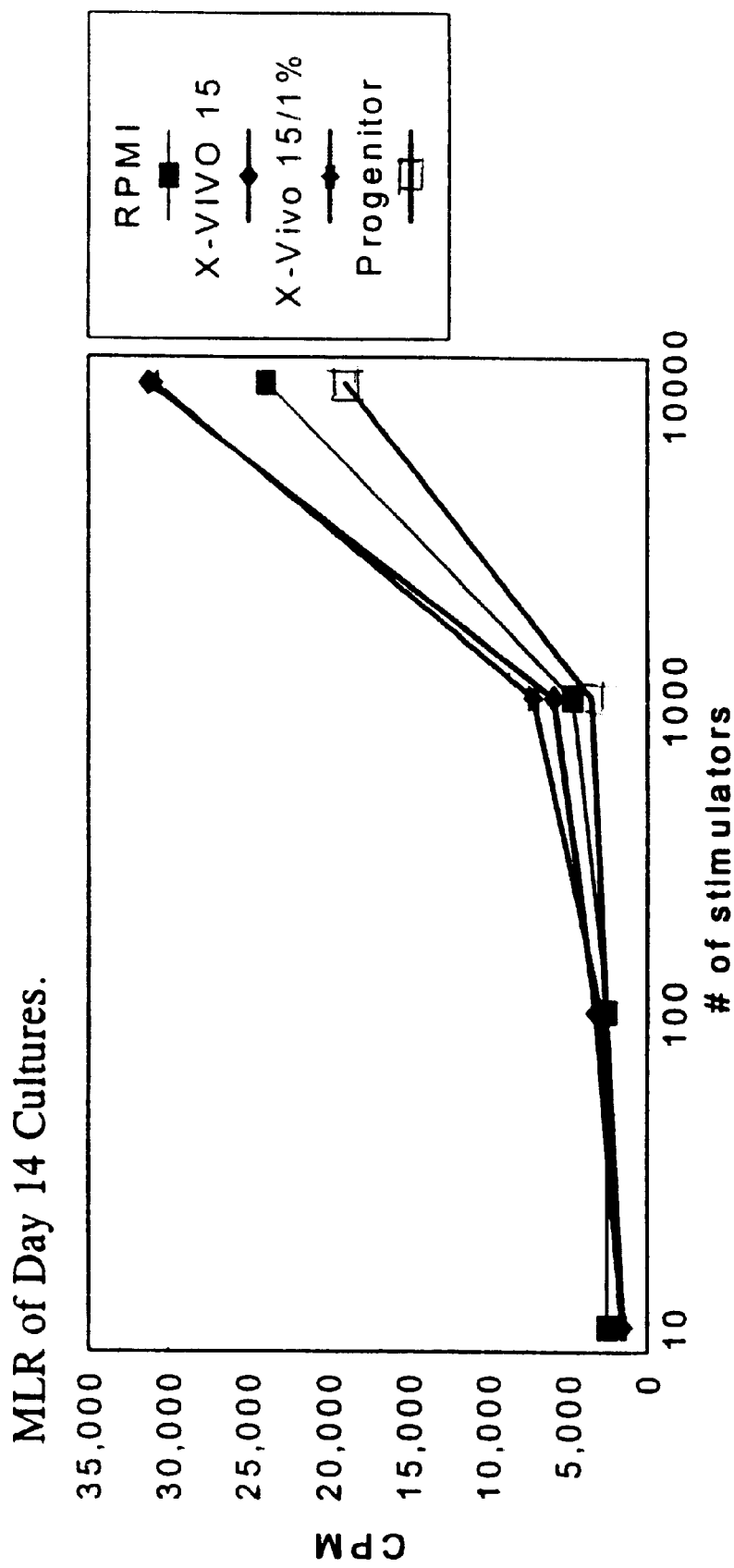
FIG. 8 depicts results of mixed-lymphocyte reactions (MLRs) using dendritic cells produced by the method of the invention, as well as control methods, as stimulators of allogeneic T-cells.

The invention provides a method for producing human dendritic cells (DC) for therapeutic purposes by culturing mononuclear cells in a medium containing at least one agent selected from the group consisting of calcium ionophores, theophylline, prostaglandin E1, dibutyryl cyclic AMP, Vitamin D3, Vitamin E, retinoic acid, and fatty acids, and maintaining the culture until it is enriched for DC. Generally, the culturing and maintaining comprise about 4–14 days in duration.

Alternatively, an enriched population of DC can be culture-derived from adherent cells. Using this embodiment of the invention, mononuclear cells are first incubated in the culture container for a time sufficient to allow a subset of cells to adhere to the polystyrene inner surface of the container. Preferably, the incubation time is at least 1 hour, more preferably 2 hours, but could be up to 18 hours. Then the non-adherent cells are removed, and those cells which adhere to the polystyrene inner surface are further cultured as described above.

Enrichment for DC is evidenced by at least about 2.5% of total cells exhibiting DC morphology, namely DC processes.

The identity of DC can also be evidenced by expression of at least one antigen selected from CD80, CD86, and CD1a, on at least 2.5% of the total cell culture population.

The invention further provides a method to produce antigen-pulsed dendritic cells for therapeutic use by culturing mononuclear cells as described above, and then contacting the cells with an antigen. The antigen may be a viral antigen, a tumor antigen, or any other antigen to which an immune response is desired.

The invention also provides a method for producing antigen-specific T-cells by co-culturing antigen-pulsed dendritic cells with T-cells to produce antigen-specific T-cells.

DETAILED DESCRIPTION OF THE INVENTION

The method begins with providing mononuclear cells (MNC) from the blood or bone marrow of the patient or an HLA-matched donor. Herein, the term MNC includes monocytes, lymphocytes, stem and progenitor cells, including CD34+ cells. The term MNC excludes granulocytes (neutrophils, basophils, acidophils), platelets, and red blood cells. The term "HLA-matched" refers to an individual who expresses at least several major histocompatibility complex (MHC) genes in common with the intended recipient. Each individual expresses at least seven different MHC proteins on his cells. Allogeneic MHC molecules are highly immunogenic and will trigger rejection of the grafted cells if there are too many mismatches. Whether or not two individuals are HLA-matched is 95/24969; U.S. Pat. No. 5,536,475; WO 91/16116; U.S. Pat. No. 5,240,856; WO 92/07243; WO 95/05843; WO 95/02685; U.S. Pat. No. 5,411,863.

MNC or pre-selected CD34+ cells are first suspended in medium containing at least one agent selected from the group consisting of calcium ionophores, theophylline, prostaglandin E1, dibutyryl cyclic AMP, Vitamin D3, Vitamin E, retinoic acid, and fatty acids. An example of a useful calcium ionophore is A23187. A fatty acid can be selected from the group consisting of linoleic acid, palmitic acid, stearic acid, eicosanoic acid, palmitoleic acid, oleic acid, linolenic acid, and arachidonic acid.

Any of the above mentioned agents can also be used in combination or serially with one or more cytokines or hematopoietic growth factors. The advantage of the invention is that it provides a means to substitute a common molecule for an individual cytokine which may be too expensive, unavailable, or otherwise unsuitable for clinical use. A cytokine can be selected from IL-4, GM-CSF, TNF-α, or any other cytokines known to be active in the hematopoeitic system. IL-4 is thought to promote the proliferation of dendritic cells by supressing the growth of monocytes, thus leaving more space and resources for the proliferation of DC, and possibly leaving more progenitors free to differentiate along the DC line. GM-CSF increases the growth and differentiation of DC along with granulocytes and macrophages. If it is desired to first select CD34+ cells, they can be cultured initially with GM-CSF to cause their proliferation, and subsequently cultured with one or more of the above named agents to promote differentiation into DC. TNF-α suppresses determined prior to the graft procedure by standard tissue typing techniques using antisera-binding to their blood cells, or by mixed lymphocyte reactions (MLR). Ideally, the donor and recipient will be completely HLA-matched, which can occur fortuitously among full siblings. However, it may not be possible to locate a completely matching donor, in which case the clinician will determine the closest HLA-matched donor available. Herein, the term "HLA-matched donor" is defined as an individual chosen by a clinician, on the basis of HLA tissue typing, as an appropriate donor for the individual patient.

MNC can be derived from bone marrow, peripheral blood, or umbilical cord blood. Since obtaining bone marrow cells entails general anesthesia, it is preferable to obtain peripheral blood cells via leukapheresis, which is a non-invasive procedure performed without anesthesia. The patient or donor may undergo a treatment with cytokines and/or chemotherapeutic agents prior to cell collection, which agents mobilize CD34+ stem cells from the bone marrow into the peripheral blood. However, it is not absolutely necessary to administer mobilizing agents to the donor; sufficient DC can ultimately be produced from non-mobilized peripheral blood, using the method of the invention. Following blood cell collection by leukapheresis, MNC are isolated by density gradient centrifugation and can be used directly in the culture system of the invention. Alternatively, CD34+ stem cells can be pre-selected from the MNC population using an antibody against CD34 in combination with various selection means to form the starting population for DC production. Various means for CD34+ cell selection are described in the following patent documents: WO 95/34817; EP 438 520; WO the growth of myeloid progenitors, such as granulocytic and macrophage progenitors, while allowing the growth of DC.

In practicing the present invention, suitable base medium is preferably chosen from among the commercially available serum-free, animal protein-free base media such as X-VIVO 10™ or X-VIVO 15™ (BioWhittaker, Walkersville, Md.), Hematopoietic Stem Cell-SFM media (GibcoBRL, Grand Island, N.Y.) or can be of any formulation which is favorable to hematopoietic cells. Serum-free media are described in the following patent documents: WO 95/00632; U.S. Pat. No. 5,405,772; PCT US94/09622. The serum-free base medium will generally contain clinical grade human serum albumin in a concentration of about 0.5–5%, usually about 1.0% (w/v). Clinical grade albumin derived from human serum, such as Buminate® (Baxter Hyland, Glendale, Calif.), is so highly purified and isolated from other serum components that it is herein considered serum-free.

The MNC or CD34+ cell suspension is preferably cultured in a container having at least one inner growing surface of polystyrene. In an alternative embodiment of the invention, an enriched population of DC can be culture-derived by first allowing the starting cell suspension to incubate in the container for about 1 to 2 hours, or even up to about 18 hours. Then, cells which do not adhere to the polystyrene inner surface are removed, and the adherent cells are further cultured as described below.

Conventional polystyrene tissue culture plates and flasks such as those available from Corning (Corning, N.Y.) will serve to promote DC growth using the system of the present invention. However, these culture containers are not gas permeable and must be maintained in an incubator with their caps open or their lids offset to allow $O_2$ and $CO_2$ equilibration with the requisite gas mixture in the incubator environment. Moreover, manipulation of these containers necessitates open handling and transfer of media and cells because the containers cannot be maintained in a closed fluid path-system. It is preferable to culture the MNC or CD34+ cell suspension in a gas-permeable container with an inner growing surface of polystyrene. This type of container is exemplified by the PL2417 container (Baxter Healthcare Corporation) which is described in co-owned pending application U.S. Ser. No. 08/549,632 (PCT US95/13943) which is herein incorporated by reference. Specifically, the sections herein incorporated by reference are in U.S. Ser. No. 08/549, 632, filed Oct. 27, 1995, on p. 6, line 14 through p, 16, line 26, which sections encompass enabling descriptions of gas-permeable culture containers having at least one inner growing surface of polystyrene.

A gas-permeable culture container offers the advantages of a closed fluid path culture system whereby the cell suspension may be added to the culture container via a sterile-connect port. Ideally, the entire cell collection, and preselection if desired, is conducted in a closed fluid path system such as the CS3000®/Isolex®300i (Baxter Immunotherapy, Irvine, Calif.) which then is aseptically connected to the gas-permeable container for the transfer of cells into the container. The culture media can then be continuously perfused through the container, or periodically refreshed, via sterile connect ports and sterile tubing systems. The cell culture within the gas-permeable container can be maintained in the gas-regulated atmosphere of the incubator without exposure to environmental hazards such as microorganisms which could otherwise be introduced into the culture when the cells are originally introduced to the container or when the medium is refreshed. Throughout the culture period, samples of the cultured cells can be aseptically drawn off from the container through sterile-connect ports for analysis. As described below, antigens and/or T-cells can be added to the DC culture via sterile-connect ports. Likewise, when the DC culture, plus or minus T-cells, is ready for harvest, the cells can be aseptically drawn off for closed-system washing and further processing. Ultimately, concentration into an infusible medium such as Plasma-Lyte® (Baxter IV Systems, Round Lake, Ill). can be carried out aseptically via sterile-connect ports, and the washed and concentrated DC/T-cells can be infused directly via the patient's intravenous line without exposing the cells to the environment, or the health-care workers to the cells. Herein, the term "closed fluid path system" refers to an assembly of components, each of which is closed to the ambient environment, and each of which is provided with means for effecting sterile connections among the components.

Whether semi-open or gas-permeable closed containers are used, the cells are maintained within the culture system until the culture is enriched for DC. Generally, a culture is considered enriched for DC when at least about 2.5% of the total cells are DC. This represents about a 25-fold enrichment over the normal cellular composition of peripheral blood, where the percentage of DC is about 0.1%. Typically, the culture is maintained for about 4–14 days, preferably about 7 days, to achieve the desired degree of DC enrichment. The absolute number of DC in the enriched culture will depend on the number of starting MNC in the culture, and the duration of culture. When cells are obtained by leukapheresis, a 1.5 hour procedure yields about $1–3\times10^9$ MNC from a non-mobilized donor. An apheresis product from a mobilized donor can yield about $2–6\times10^{10}$ MNC, about 1.0%–7.0% of which are CD34+ cells. For example, using the method of the invention, and maintaining the culture for about 7 days, a number of DC appear in the DC-enriched culture which is equal to one-tenth the starting number of MNC which were originally placed in culture. In other words, if two million DC are desired, 20 million MNC are provided in the starting culture. Thus it is possible to use all or part of the MNC from an apheresis product to produce the desired number of DC. If even more DC are desired, one can collect, freeze and store several leukapheresis products from the donor until the desired starting number of MNC cells is achieved. However, it is expected that a single leukapheresis product will provide sufficient starting cells for most therapeutic purposes.

Dendritic cells possess characteristic processes which are evident on their surfaces upon inspection under a microscope when the cells are stained with a common histological stain. Samples of the culture are prepared on cytospin slides and stained with any conventional stain that enables visualization of the processes, such as Wright-Giemsa, hematoxylin, or an immunohistochemical stain. Examples of dendritic-cell processes are indicated with hollow arrows in FIGS. 1–6. In FIGS. 1–4 and 6–7, these processes take the form of "veils", which are feathery, barely outlined projections which usually appear to be more lightly stained than the cytoplasm. Such veils on dendritic cells are also shown in prominent publications such as the cover of *Blood* Volume 87, Jan. 15, 1996. Other types of well-recognized dendritic-cell processes are indicated with certain hollow arrows in FIG. 7. These processes take the form of ruffles or dendritic projections which may appear to be stained as densely as the cytoplasm, depending on the histological stain used. Herein the term "dendritic cell" refers to a cell which exhibits dendritic cell processes. Thus, enrichment of a culture for DC is evidenced by at least about 2.5% of the total cells exhibiting dendritic cell processes.

The identity of DC in the culture can also be evidenced by the expression of at least one antigen selected from CD80, CD86, and CD1a, on at least 2.5%. of the cultured cell population. CD80, also known as B7–1, is a highly glycosylated single-chain protein of about 60 kDa which is constitutively expressed on DC, activated B cells and monocytes (In: Schlossman, S F, et al., eds., *Leukocyte Typing V*, Oxford University Press, Oxford, 1995, p.682–684; Larsen, C P, et al., *J Immunol* 152:5208–5219, 1994; Hathcock, Kans., et al., *J Exp Med* 180:631–640, 1994). CD86, also known as B7-2, is an 80 kDa glycoprotein which is constitutively expressed on DC as well as on activated B cells and monocytes (In: Schlossman, SF ibid p. 703–705; Larsen, C P et al., supra; Hathcock, Kans., et al., supra). Although CD80 and CD86 may have other functions, they are known as ligands for the T-cell CD28 antigen. Interaction of CD80 and/or CD86 on antigen-presenting cells with CD28 on T-cells allows the close association of the two cell types required for internal signaling and activation of the T-cell. CD1a is a 49 kDa glycoprotein associated with B2-microglobulin which is not present on peripheral blood T and B lymphocytes, monocytes, or normal bone marrow mononuclear cells, but is present on cortical thymocytes and on Langerhans cells, which are considered DC of the epidermis (Bounsell L, et al., In: Reinherz E L et al., eds, *Leukocyte Typing II: Human T Lymphocytes*. New York Springer-Verlag; 1986:289–302; Martin L H, et al., *PNAS USA* 1987; 84:9189).

Antibodies to CD80, CD86, and CD1a, suitable for immunohistochemical staining and phenotyping by flow-cytometry, are widely available from companies such as Immunotech (Westbrook, Me.), Coulter (Hialeah, Fla.), Becton Dickinson (San Jose, Calif.), Ancell (Bayport, Minn.), BioSource (Camarillo, Calif.), and Serotec (Indianapolis, Ind.).

The function of a DC culture may be confirmed by conducting a mixed-lymphocyte-reaction (MLR) in which a number of cells from a culture containing DC is mixed with allogeneic T-cells, and the subsequent proliferation of the T-cells is assayed. For instance, a given ratio of putative DC to allogeneic T-cells is said to be 30–100 times more active in a MLR, as assessed by $^3$H-thymidine incorporation in the T-cells, when compared with a comparable ratio of MNC to allogeneic T-cells. (Steinman, R M, *Annu Rev Immunol* 9:271–296, 1991; Steinman, R M, et al., *CRC Crit. Rev. Immunol.* 5:331–348, 1985).

Once the desired number of DC is present in the culture, the DC can be "pulsed" with an antigen. Herein the term "antigen-pulsed dendritic cells" refers to DC which have been contacted with an antigen. It is generally believed that dendritic cells require a few hours, or up to a day, to process the antigen for presentation to naive and memory T-cells. It may be desirable to pulse the DC with antigen again after a day or two in order to enhance the uptake and processing of the antigen.

Figure 9:
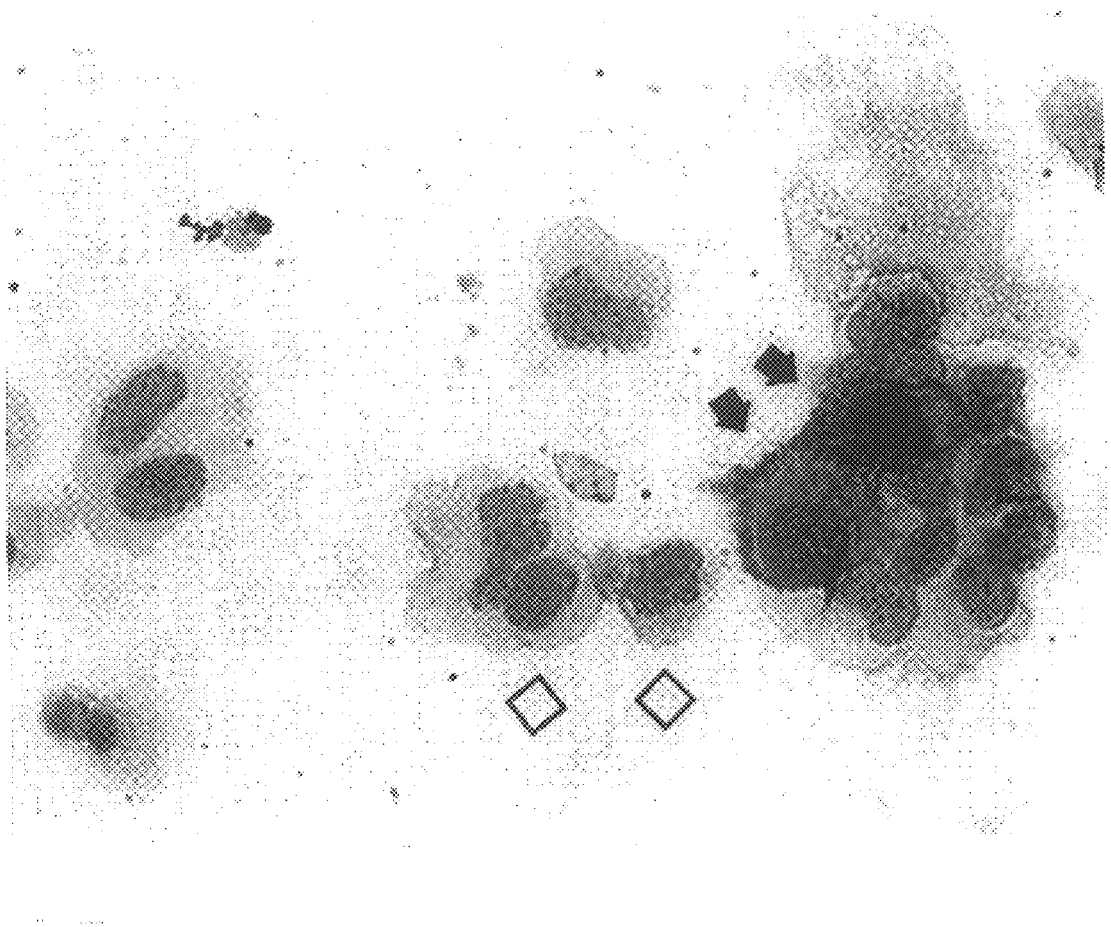
FIG. 9 shows dendritic cells produced by the method of the invention which were pulsed with tetanus toxin antigen peptide (TT), then co-cultured with autologous T-cells according to the method of the invention for seven days. Solid arrows indicate two dendritic cells which are prominently stained by an antibody to TT using immunohistochemistry. Hollow diamonds indicate T-cells.

Once the DC has engulfed and processed the antigen, it is termed an "antigen-primed DC". Evidence of antigen-priming can be seen in DC which have been in the presence of the antigen for some time, then processed through immunohistochemistry for staining with an antibody to the specific antigen used for pulsing. Generally, it will be evident that the antigen is located throughout the cytoplasm of the DC, and may be especially concentrated along the plasma membrane of the DC (see FIG. 9).

Antigens are chosen for a specific purpose such as preparing an antigen-specific DC or T-cell composition as a vaccine or a therapeutic agent against a specific cancer cell and/or virus or a bacterial infection. For instance, antigens of hepatitis B virus (HBV), hepatitis C virus (HCV), the various glycoproteins of human immunodeficiency virus (HIV), or bacterial antigens can be used to pulse DC, thereby producing specific antigen-primed DC. Antigen-primed DC can be infused directly to the patient where they are expected to interact with T-cells in vivo to induce the desired immune response (Hsu, FJ, et al., supra). Antigen-primed DC can also be co-cultured with T-cells; the co-culture product will be antigen-specific T-cells useful for infusion to a patient to prevent or ameliorate infection by the specific pathogen. Similarly, antigens of Epstein-Bass virus, which causes lymphomas, or papilomavirus, which causes cervical cancer, can be used in this system to produce antigen-specific DC and/or T-cells useful for prevention or amelioration of the viral infections and their associated cancers. Antigens of HER2/neu or chorio-embryonic antigen (CEA) can be used to produce antigen-specific DC and/or T-cells for treatments against cancers of the breast, ovary, pancreas, colon, prostate, and lung which express these antigens. Similarly, mucin-type antigens such as MUC-1 can be used against various carcinomas; the MAGE, BAGE, and Mart-1 antigens can be used against melanomas. It is expected that such a treatment will be tailored to a specific cancer patient based on which antigen(s) are expressed in the patient's cancer cells, as predetermined by surgical biopsy or blood cell sample followed by immunohistochemistry. On the other hand, treatment directed against viral or bacterial antigens can be based on the expected exposure of the subject to specific pathogens in high-risk occupations such as health care. It is also conceivable that DC could be used for tolerance induction when transplant of allo- or xeno- cells or organs is contemplated.

The antigen-pulsed DC population can then be washed, concentrated, and infused directly into the patient as a type of vaccine or treatment against the pathogen or tumor cells from which the antigen originated. This type of use is exemplified by reports from the Ronald Levy group on their treatment for B-cell lymphoma wherein an immune reaction to the B-cell antigen was induced by as few as two to three million antigen-pulsed DC after only one infusion (Hsu, FJ, et al., supra). The antigen-pulsed DC are expected to interact with naive and/or memory T-lymphocytes in vivo, thus causing them to recognize and destroy cells displaying the antigen on their surfaces. It is within the scope of the present invention to optimize the number of antigen-pulsed DC per infusion, and the number and timing of infusions. In general, there will be at least 2 million antigen-pulsed cells per infusion, but fewer cells may also induce the desired immune response.

Yet another use for culture-derived DC lies in the field of gene therapy. DC can be genetically modified ex vivo by infection or transfection using a viral vector, for instance, carrying a foreign or corrective gene. For example, DC can be genetically modified to express cytokines, or increased co-stimulatory molecules or adhesion molecules. The genetically modifed DC are then infused to the patient, and are expected to express the transfected gene in vivo, thereby enhancing their therapeutic effect.

Alternatively, or perhaps additionally, the antigen-pulsed DC culture may be co-cultured with T-lymphocytes to produce antigen-specific T-cells. Herein the term "antigen-specific T-cells" refers to T-cells which have been contacted by an antigen-primed DC and thus caused to proliferate as well as to develop the ability to attack cells having the specific antigen on their surfaces. Such T-cells, known as cytotoxic T-cells, lyse target cells by releasing toxic enzymes such as granzymes and perforin onto the surface of the target cells or by effecting the entrance of these lytic enzymes into the target cell interior. Cytotoxic T-cells may express the protein antigen known as CD8 on their surface membranes. The CD8 antigen is a determinant on the 32-kDa α-subunit of a disulfide-linked bimolecular complex (In: Knapp W, Dörken B, Gilks W R, et al., eds. *Leucocyte Typing IV: White Cell Differentiation Antigens*. Oxford: Oxford University Press; 1989:342–346). The CD8 antigenic determinant on a cytotoxic T-cell binds to a Class I major histocompatibility (MHC) molecule in association with a target antigen on a cancer cell or virally infected cell, thus increasing adhesion of the T-cell to the target cell and facilitating lysis of the target cell. Certain T-cells which express the antigen CD4, known as "helper" T-cells, can also help promote specific cytotoxic activity. The CD45RO antigen is present on certain memory T-cells within the CD4 and CD8 populations, and is thought to be essential for lymphocyte activation (In: Schlossman, SF, et al., eds., *Leucocyte Typing V*, Oxford University Press, Oxford, 1995, p. 386–399; Trowbridge, LS, et al., *Annu Rev. Immunol* 12:85–116, 1995). One can use the non-targeted (non-selected) fraction of a CD34+ selection as a starting source of T-cells, or one can pre-select T-cells expressing antigens such as those described above for starting the co-culture.

The T-cells can be derived from the same donor whose MNC yielded the DC, which can be the patient or an HLA-matched individual as described above. Alternatively, the T-cells and DC can be derived from two different HLA-matched individuals.

In order to optimize the number and antigen-specificity of the T-cells, a second portion of antigen-pulsed DC can be added to the co-culture after one or several days of the original co-culture. After the antigen-specific T-cells in the co-culture have proliferated to the desired number, they can be washed, concentrated and infused to the patient. Alternatively, certain sub-populations of T-cells can be selected from the co-culture prior to infusion. Well known means for selecting cells displaying a specific antigen on their surfaces have been described above for CD34+ cells. The same principles can be applied to selecting sub-populations of CD8+, CD4+, and/or CD45RO+ cells. These selected cells can then be washed, concentrated, and infused to the patient to fight the specific virally infected or cancer cells.

When DC are intended to be used as stimulators of T-cells ex vivo, the number of antigen-pulsed DC needed is in the range of about two to about 100 million. This range is based on the assumption that a ratio of 1:50 to 1:10 DC:T-cells is required for efficient activation of the T-cells. It is estimated that about 100 million to 1 billion antigen-specific T-cells are required to achieve the desired cell-killing activity in vivo, and that activated T-cells will comprise about 10%; of the total T-cells in a co-culture. Therefore, about one billion to ten billion T-cells are needed in the final co-culture. Assuming a proliferation index (PI) of 10 for the T-cells, about 100 million to about one billion T-cells are seeded in the beginning co-culture. Thus, at a ratio of 1:50, DC:T-cells, a range of two million to 20 million antigen-pulsed DC are needed in the co-culture. At a ratio of 1:10, DC:T-cells, ten million to 100 million antigen-pulsed DC are needed in the co-culture.

The following examples are offered to further illustrate the invention.

EXAMPLE 1

Dendritic Cells Culture-derived from Mononuclear Cells

Whole blood from healthy human donors was obtained from several sources. Mononuclear cells from apheresis products were obtained from the Fenwal Division, Baxter, Round Lake, Ill. When CD34+ cell pre-selection was employed, certain donors with cancer conditions had been pre-treated with chemotherapeutic agents or G-CSF, or both, to mobilize stem cells into their peripheral blood. For CD34+ cell pre-selection, healthy volunteers also received pre-treatment with G-CSF in order to mobilize stem cells from their marrows into their peripheral blood for collection.

Equipment and Materials:

FACSort™ or FACScan™ flow cytometer, Becton Dickinson, San Jose, Calif.

Mouse IgG1 FITC, Mouse IgG1 PE, Goat anti-mouse IgG FITC, Becton Dickinson.

Goat anti-mouse F(ab)'2 IgG (H & L chains) FITC; Goat anti-mouse F(ab)'2 IgG (H & L chains) PE, Immunotech, Westbrook, Me.

Anti-CD3 FITC, Anti-CD3 PE, Becton Dickinson.
Anti-HLA-DR PE, Becton Dickinson.
Anti-CD1* FITC, Biosource, Camarillo, Calif.
Anti-CD80, Immunotech.
Anti-CD86 PE, Ancell, Bayport, Minn.
Anti-CD54 PE, Becton Dickinson.
Anti-CD45 PE, Coulter, Hialeah, Fla.
Anti-HLA-ABC, Serotec, Indianapolis, Ind.
RPMI 1640; X-VIVO 15 ™medium ; Fetal Calf Serum (FCS), BioWhittaker, Walkersville, Md.
Human Albumin (HA), Baxter Hyland Division, Glendale, Calif.
Dulbecco's Phosphate Buffered Saline-Magnesium and Calcium free, BioWhittaker.
PL732® Lifecell® Flasks; PL2417 gas permeable culture containers, Baxter, Round Lake, Ill.
75 cm$^2$ polystyrene tissue culture flasks, Corning, Corning N.Y. IL-4, Genzyme, Cambridge, Mass.
Leukine™ (sargramostim) human GM-CSF, Immunex, Seattle, Wash.
TNF-α, R&D Systems, Minneapolis, Minn.
SCF, Genzyme.
Ficoll-Paque® density gradient prepration, Pharmacia, Uppsala, Sweden.
L-glutamine, Sigma, St. Louis, Mo.
Sheep Red Blood cells, BioWhittaker.
Anti-CD3 mAb (MT-301); Anti-CD4 mAb (MT-415); Anti-CD8 mAb (MT-494), Baxter Immunotherapy, Munich, Germany.
Immune Globulin Intravenous (Human) Gammagard® S/D, Baxter
Hyland Division. Dynabeads® M-450 magnetic beads, Dynal, Oslo, Norway.
ACK Lysis Buffer, Cytofunnels™, Shandon, Pittsburgh, Pa.
96 well round bottom plate, Corning.
$^3$H-thymidine, Amersham, Cleveland, Ohio.
Mitomycin C, Sigma, St. Louis, Mo.
Tetanus Toxoid, Wyeth Laboratories Inc., Marietta, Pa.
Wright-Geimsa Stain, EM Diagnostics Sys., Gibbstown, N.J.
Trypsin, Metrizamide, 2-Aminoethylisothiouronium Bromide (AET), Sigma.

Methods

Preparation of Mononuclear Cells from Whole Blood:

Blood was diluted 1:2 with phosphate-buffered saline, calcium-and magnesium-free (PBS-CMF) and aliquoted into 50 ml polypropylene centrifuge tubes (40 ml each). Each tube was provided an underlayer of 10 ml ficoll, then centrifuged at 400 xg for 20 min. at room temperature. The interface was removed from each tube and placed into 50 ml tubes, then washed with PBS-CMF at 400 xg for 10 min. at room temperature. The washed mononuclear cells (MNC) were then resuspended into the desired volume.

Preselection of CD34+ cells was conducted using an Isolex® apparatus (Baxter Immunotherapy, Irvine, Calif.) per manual instructions.

Culture of MNC and CD34+ Cells:

Either non-selected MNC or pre-selected CD34+ cells were cultured in either RPMI 1640 supplemented with 10 fetal calf serum (FCS) and 2 mM L-glutamine, or X-VIVO 15™ serum-free medium, or X-VIVO 15™ serum-free medium containing 1% HA. Cultures were initiated at 5×10$^5$ cells/ml. GM-CSF was used at concentrations ranging from 500 to 5000 U/ml. IL-4 was used at concentrations of 1000 U/ml and 1400 U/ml. TNF-α was used at 100 ng/ml and SCF was used at a concentration of 25 ng/ml.

Cells were cultured in polystyrene tissue culture flasks (75 cm $^2$) or polystyrene tissue culture plates (collectively both polystyrene flasks and plates will be denoted as "flasks"). Cells were also cultured in PL732® Lifecell® flasks or PL2417 gas permeable containers. The PL7320® Lifecell® flasks are composed of a polyolefin blend of EVA, polypropylene, and Kraton. The PL2417 containers are composed of a multilayer, gas-permeable film, with a thin layer of polystyrene on the inner surface. Culture containers were filled with cell cultures by either spiking inlet ports with sample site couplers then aseptically injecting cultures into the bags using a syringe and needle (PL2417) or a syringe with its plunger removed from the barrel was attached to the female sample tubing (PL732® flasks) and cultures were then aseptically poured into the bag, using the syringe as a funnel. Cells were cultured for up to 7 or 8 days in 5% $CO_2$, ambient $O_2$, 37° humidified incubator. A solution tranfer pump, such as the Lifecell® Solution Transfer Pump sold by the Baxter IV Systems division in Round Lake, Ill., can be used for the efficient transfer of solutions.

Immunomagnetic Depletion of T Cells:

MNC were prepared from whole blood. MNC were resuspended to a concentration of 5×10$^7$ cells/ml in PBS-CMF containing 1% HA and 0.1% Human immunoglobulin (HIg) (PBS/1% HA/01% HIg). Anti-CD4 and anti-CD8 or anti-CD3 monoclonal antibodies (mAb) were added to a final concentration of 10 ug/ml each. Cells were rotated at 4° C. for 30 minutes then washed 3 times in PBS-CMF in a centrifuge. Cells were resuspended to 5×10$^7$ cells/ml in PBS/1% HA/01% HIg.

Sheep anti-mouse Ig magnetic beads were washed by placing them in a 15 ml polypropylene tube then placing the tube next to a magnet. The beads were allowed to adhere to the side of the tube closest to the magnet, then the supernatant was removed. Fresh PBS-CMF was added, the tubes were vortexed and then placed next to the magnet again. The supernatant was decanted. The number of beads to be used was calculated as follows:

(% of T cells in MNC)(# of total MNC)(10 beads/cell) Cells were added to the washed beads and rotated for 30 min. at 4° C. The cell/bead complexes were removed with a magnet. Both T cells and non-adherent cells were washed with PBS-CMF and resuspended in the indicated medium at the appropriate concentration.

Phenotyping of Cultured Cells:

One million cells were transferred into three 12×75 mm polypropylene tubes. One ml of PAB was added to each tube, and cells were collected by centrifugation for 3 min at room temperature at HIGH setting (1,000 xg) using a SERO-FUGE II. The supernatants were decanted, the excess liquid was blotted on absorbent paper and the tubes were vortexed gently to loosen the cell pellets. The cells were stained by adding conjugated and pure antibodies as follows (the choice of stains varied with each experiment):

| Pure | FITC conjugated | PE conjugated |
|---|---|---|
| | Isotype IgG | Isotype IgG |
| | Isotype IgG/ | Isotype IgG/GAM |
| | Goat anti-mouse | |
| | IgG (GAM)* | |
| | CD14 | HLA-DR |
| | CD1a | HLA-DR |
| | CD1a | HLA-ABC |
| | CD1a | CD14 |
| | CD1a | CD86 |
| | CD80 | CD54 |

*GAM used was either whole IgG (Becton Dickinson) or F(ab)'$_2$ (Immunotech). The pure antibodies were added first, and the tubes were incubated for 15 minutes on ice.

Step A. One ml of PAB was added to each tube and the tubes were vortexed to mix. The cells were collected by centrifugation for 3 min at room temperature at HIGH setting using the SERO-FUGE II, then the supernatants were decanted, the excess fluid was blotted off and the tubes were vortexed gently to loosen the pellets.

The GAM was added and the tubes were incubated for 15 minutes on ice. Then step A was repeated.

The PE conjugated antibodies were added and the tubes were incubated on ice for 15 min. Then step A was repeated.

The cells were resuspended in 500 ul PAB. The cells were held on ice until they were analyzed with the flow cytometer.

Viability Determination: Prior to acquisition, 5 ul propidium iodide (PI) was added to each tube for use as a viability check. The cells were vortexed and acquired within 10 min of PI addition.

Analysis Using the Becton Dickinson LYSIS™ II Software:

A file collected on isotype control stained cells was displayed using the forward scatter versus side scatter dot plot. The side scatter versus FL3 dot plot of the same file (isotype control) was displayed and a viability region (R1) was set around the FL3 negative cells. These were the propidium iodide negative (viable) cells. With the viability region (R1) applied, the FL1 versus FL2 dot plot of the isotype control sample was displayed. The quadrant cursors were set so that the majority of the FL1 and FL2 negative cells were located in the lower left quadrant. With the viability region (R1) applied, the FL1 versus FL2 dot plot of the FITC and PE stained cells was displayed. The quadrants described above were copied. The %FITC+/PE+ cells were determined by subtracting the %/FL1+/FL2+ the isotype control (upper right quad) from the %FL1+/FL2+ (upper right quad) of the FITC/PE stained sample. This was subsequently done with any FITC/PE combinations needed by subtracting the % positive in the isotype control.

Preparation of Cytospin Slides and Wright-Giemsa staining:

Cytofunnels were attached to microscope slides. 50,000 to 100,000 cells were removed from each culture and resuspended in approximately 100 to 200 ul of PBS-CMF. Slides were placed in the Cytospin® centrifuge and spun at 100 rpm for 4 min. Cytofunnels were removed from the slides and the slides were air dried for 1 minute. Ten drops of Wright-Geimsa stain were placed onto each slide and allowed to fix for 1 to 2 minutes. Ten drops of water were added to each slide and allowed to sit for 2 to 4 minutes. The slides were rinsed and air dried.

Reading of Cytospin Slides: Slides were read under phase contrast microscopy, 40× and 60× oil magnification. One hundred cells were identified and characterized morphologically as either dendritic cells or non-dendritic cells (lymphocytes and monocyte, or CD34+-derived cells in those cases). Digital images were taken using a color monitor and color video printer.

Preparation of Mixed Lymphocyte Reactions (MLR):

MLR's were setup using T cells as responders and dendritic cell enriched cultures as antigen presenters. Sheep red blood cells were prepared and used to erythrocyte rosette T cells from a MNC preparation as described in "Current Protocols in Immunology", John Wiley & Sons Inc, 1995. Vol. 2, 7.2.1–7.2.4. Erythrocyte+(E+) T cells were resuspended to $1 \times 10^6$ cells/ml in RPMI 1640/10% FCS. Dendritic cells were resuspended to $1 \times 10^6$ cells/ml in RPMI 1640/10% FCS and mitomycin C was added at 25 ug/ml to inhibit proliferation. The tubes were incubated at 37° C. for 30 min. then washed 3 times with PBS-CMF/1% HA. On a 96-well round bottom polystyrene tissue culture plate, dendritic cells were added at 10,000 cells/well, 1000 cells/well, and 100 cells/well. To each of these wells, 100,000 T cells were added. The appropriate control wells were also prepared. Plates were incubated for 4 or 5 days at 37° C.

Each well was pulsed with 1 uCi of $^3$H-thymidine in RPMI 1640/10% FCS. Plates were incubated overnight at 37° C.

Plates were harvested onto glass fiber filter strips using a cell harvester. Discs were placed into scintillation vials containing scintillation cocktail and samples were counted using a beta radiation counter.

RESULTS

PL2417 culture containers were evaluated for their ability to support dendritic cells. PL2417 containers are a newly developed product of Baxter Healthcare Corporation which are made from a flexible, gas-permeable multilayer film, with a thin layer of polystyrene on the inner growing surface. These PL2417 containers are compatible with a closed fluid path culture system. In 3 experiments, MNC's were cultured in X-VIVO 15™/1% HA containing 2500 U/ml GM-CSF and 1000 U/ml IL-4 in PL732® Lifecell® Flasks, PL2417 culture containers, and polystyrene tissue culture flasks. These were compared to cells cultured in polystyrene flasks containing RPMI/10% FCS, IL-4 and GM-CSF. Cells were cultured for 8 days at which time all cultures contained a non-adherent fraction as well as an adherent fraction. The adherent fraction was removed via trypsinization from the culture vessels. Both fractions from each culture were analyzed for expression: CD1a, HLA-DR, CD86, CD80, and CD54 (ICAM-I). There were not enough adherent cells in the PL7320 ® or PL2417 flasks/bags to phenotype. Cytospins were prepared from each fraction and differentials were read. Table 1 represents the mean percentage of each phenotype (n=3) as well as the mean percent of Non-DC and DC, as determined morphologically, at days 0 and 8.

Table 1. Evaluation of PL2417 flask and Comparison of Adherent and Non-Adherent Cell Populations, and Examination of Antibodies to DC's.

TABLE 1

| Day | Condition | CD1a+/DR+ | CD80+/CD54+ | Non-DC | DC |
|---|---|---|---|---|---|
| 0 | All | 0.43% | 6.43% | 100% | 0% |
| 8 | X-VIVO15/1% HSA, PL732 | 0.00% | 0.00% | 99% | 1% |
|   | X-VIVO15/1% HSA, PL2417 | 0.00% | 3.46% | 90% | 10% |
|   | X-VIVO15/1% HSA, flask | 0.00% | 3.57% | 88% | 12% |
|   | 10% FCS/RPMI, flask | 0.00% | 0.00% | 93% | 7% |
|   | X-VIVO 15/1% HSA, flask, adherent | 5.12% | 6.05% | 76% | 24% |
|   | 10% FCS/RPMI, flask, adherent | 0.00% | 27.52% | 81% | 19% |

In one experiment, MNC were depleted of CD3+ cells using magnetic bead technology. The cells were cultured in X-VIVO 15™ plus 1000 U/ml IL-4 and 1000 U/ml GM-CSF in PL732® and PL2417 culture containers. These were compared to CD3+ depleted cells cultured in RPMI/ 10% FCS plus cytokines in a polystyrene tissue culture flask. The cultures were assessed for expression of CD1a, HLA-DR, HLA-ABC, and CD14. Cytospins were prepared from each culture and differentials were read. The percentage of CD1a+/HLA-DR+ peaked at day 1 for all cultures. Viability at day 1 for all cultures was over 90%, however by day 7, only the X-VIVO 15™ PL2417 culture had a viability over 80% (Tables 2 and 3).

Tables 2 and 3. Evaluation of CD3 Depleted MNC's as the Starting Cell Population of DC Cultures.

TABLE 2

| Day | Condition | viability | Phenotype | | | |
|---|---|---|---|---|---|---|
| | | | CD1a+/ABC+ | CD1a+/DR+ | CD14+/ABC+ | CD14+/DR+ |
| 0 | All | 98.02% | 0.00% | 7.92% | 0.00% | 39.38% |
| 1 | RPMI/10% FCS, flask | 98.14% | 3.95% | 32.81% | 1.04% | 21.06% |
| | X-VIVO 15, PL732 | 94.47% | 9.11% | 34.46% | 1.31% | 22.73% |
| | X-VIVO 15, PL2417 | 94.45% | 7.88% | 26.57% | 0.64% | 19.47% |
| 7 | RPMI/10% FCS, flask | 65.51% | 5.95% | 18.15% | 0.00% | 1.79% |
| | X-VIVO 15, PL732 | 32.99% | 0.00% | 2.33% | 0.00% | 3.22% |
| | X-VIVO 15, PL2417 | 82.31% | 0.29% | 3.12% | 0.22% | 2.16% |

TABLE 3

| Day | Condition | Morphology | |
|---|---|---|---|
| | | Non-DC | DC |
| 0 | All | ND | ND |
| 1 | RPMI/10% FCS, flask | ND | ND |
| | X-VIVO 15, PL732 | ND | ND |
| | X-VIVO 15, PL2417 | ND | ND |
| 7 | RPMI/10% FCS, flask | 74% | 26% |
| | X-VIVO 15, PL732 | 97% | 3% |
| | X-VIVO 15, PL2417 | 91% | 9% |

Culture derivation of dendritic cells from CD34+ cells was evaluated. Frozen CD34+ cells selected from apheresis products using the Isolex® technology were thawed. Cells were cultured in polystyrene flasks containing either X-VIVO 15™ plus 100 ng/ml GM-CSF and 100 ng/ml TNF-α, X-VIVO 15™ plus 100 ng/ml GM-CSF, 100 ng/ml TNF-α, and 25 ng/ml SCF, RPMI/10% FCS plus 100 ng/ml GM-CSF and 100 ng/ml TNF-α, or RPMI/10% FCS plus 100 U/ml GM-CSF, 100 ng/ml TNF-α and 25 ng/ml SCF. Tables 4 and 5 show the mean percent of the total of each phenotype present in the cultures at days 0 and 8. Table 6 shows the total number of cells projected in the cultures at day 8.

Tables 4 and 5. Culture of DC from CD34+ Cells in GM-CSF, TNF-α, and SCF.

TABLE 4

| Day | Condition | Viability | Phenotype CD1a+/CD86+ |
|---|---|---|---|
| 0 | All | 98.69% | 2.14% |
| 8 | X-VIVO 15/GM/TNF | 88.01% | 15.88% |
| | X-VIVO 15/GM/TNF/SCF | 93.87% | 0.31% |
| | RPMI/10% FCS/GM/TNF | 86.08% | 0.00% |
| | RPMI/10% FCS/GM/TNF/SCF | 91.42% | 0.00% |

TABLE 5

| Day | Condition | Phenotype | | Morphology | |
|---|---|---|---|---|---|
| | | CD34+ | CD14+ | non-DC | DC |
| 0 | All | 91.91% | 5.64% | ND | ND |
| 8 | X-VIVO 15/GM/TNF | 38.61% | 10.13% | ND | ND |
| | X-VIVO 15/GM/TNF/SCF | 64.39% | 0.00% | ND | ND |
| | RPMI/10% FCS/GM/TNF | 30.70% | 1.21% | 89.00% | 11.00% |
| | RPMI/10% FCS/GM/TNF/SCF | 26.58% | 0.94% | 90.00% | 10.00% |

TABLE 6

| Day | Condition | Total Projected in Culture | | |
|---|---|---|---|---|
| | | CD1a+/CD86+ | CD34+ | CD14+ |
| 0 | All | 1.58E+05 | 6.81E+06 | 4.18E+05 |
| 8 | X-VIVO 15/GM/TNF | 6.71E+05 | 1.63E+06 | 4.28E+05 |
| | X-VIVO 15/GM/TNF/SCF | 1.89E+04 | 3.93E+06 | 0.00E+00 |
| | RPMI/10% FCS/GM/TNF | 0.00E+00 | 5.71E+05 | 2.25E+05 |
| | RPMI/10% FCS/GM/TNF/SCF | 0.00E+00 | 6.66E+05 | 2.35E+04 |

In 8 days, all the cultures decreased in numbers of CD34+ cells and the cultures containing X-VIVO 15™ m/GM-CSF/

TNF-α had increased numbers of DC+ cells. Overall, SCF did not seem to substantially help these cultures.

EXAMPLE 2

Deriving Dendritic Cells from CD34+ Selected Cells

The source of CD34+ cells was Isolex® selected products received from Baxter Immunotherapy, Irvine, Calif., previously frozen and thawed for culture, or utilized fresh. The CD34+ cells were selected from apheresis products from the peripheral blood of healthy volunteers who had been pre-treated with G-CSF to mobilize their CD34+ stem cells from their marrows to their peripheral circulation.

All materials were obtained from the companies described in Example 1 above with the following additional sources:
PROGENitor™-34 media; PROGENitorm™-34 Supplement, Gibco Life Technologies R&D, Grand Island, N.Y.
4 Well Linbro® Tissue culture plates, Flow Laboratories, MacLean Va.
PL2417 gas permeable containers, Baxter Immunotherapy Division, Round Lake, Ill.
T175 polystyrene flasks, Corning
Mouse IgG1 FITC; Mouse IgG1 PE, Becton Dickinson
Goat anti-mouse F(ab)'2 IgG (H & L chains) FITC; Goat anti-mouse F(ab)'2 IgG (H & L chains) PE, Immunotech
Anti-CD34 PE, Anti-CD14 FITC; Anti-HLA-DR, Becton Dickinson
Anti-CD80, Immunotech
Anti-CD80 PE, Becton Dickinson
Anti-CD86 PE, Ancell
X-11-FITC, Immunotech
Anti-CD3FITC/CD4PE simultest, Becton Dickinson
Anti- CD1a, Coulter
Anti- CD1a FITC, Serotec
Anti-CD1* FITC, Biosource
Anti- CD1a, Becton Dickinson
Anti-CD35, Dako
Sheep red blood cells, BioWhittaker
Pure anti-CD86, Ancell
Anti-CD35; Anti S100, Dako, #Z0311
HistoMark Streptavadin-HRP system, goat-anti-rabbit IgG (H+L), Kirkegaard & Perry, Gaithersburg, Md.
HistoMark Streptavadin-HRP system, goat-anti-mouse IgG(H+L), Kirkegaard & Perry
Peroxidase Chromagen kit (AEC); Hematoxylin; Crystal-Mount™
Biomeda, Foster City, Calif.

METHODS

Culture of CD34+ Cells

CD34 selection was performed using ISOLEX™, per manual instructions.

Frozen sources: Frozen CD34+ cells were removed from liquid nitrogen in 1 ml vials of $5\times10^6$. Vials were thawed rapidly in warm tap water and immediately transferred to a 50 ml polypropylene tube containing X-VIVO 15™ media. Cells were pelleted by centrifugation at 400 g for 7 min., washed twice with X-VIVO 15™ media, and resuspended in a final volume of 10 ml. Cells were counted using Coulter counter, 10 ml cetrimide and 20 ul of sample cells, washed a final time in 50 ml X-VIVO 15™, and resuspended in 1 ml PBS. Aliquots of this final cell suspension were then added to appropriate volumes of media, plus growth factors chosen to drive preferential differentiation of dendritic cells.

In the case of flask culture, cells were added directly to media and growth factors in the flask. The PL2417 containers were filled using a 250 ml conical tube, pouring the appropriate cell suspension into a 60 ml syringe barrel attached as a funnel to an injection port of the PL2417 container via a needle.

Fresh sources: Fresh CD34+ cells were processed in a similar manner except for the thaw and subsequent washings. Cell samples were counted on a Coulter counter in 10 ml cetrimide+20 μul of sample cells. Viability and CD34+ percentages were assessed prior to setting up the experiment via PI exclusion of dead cells, anti-CD34 PE staining, and acquisition on FACSort.

For culture plates, aliquots were removed from the source, placed in 50 ml tubes, centrifuged, and resuspended in appropriate media+growth factors, and aliquoted into the plates.

Flask and bag cultures were set up as described above for the frozen sources.

Poietic Technologies, commercial source: Cells received were frozen day 7 cells termed intermediate progenitors by Poietic Technologies, thawed and cultured in the following manner. RPMI/10FCS media was warmed. The vial of frozen cells was quickly thawed in a 37° C. water bath and the outside of the vial was cleaned with 70% ethanol. A maximum of 2 ml of cell suspension was aseptically transferred to a 50 ml conical tube. The vial was rinsed with 1 ml of media and added dropwise to the cells while gently swirling after each addition. Enough medium was slowly added dropwise to the cells until the total volume was 5 ml, while gently swirling after each addition of several drops. The volume was slowly brought up to 50 ml by adding 1 ml to the 2 ml volumes of media dropwise, gently swirling after each addition of media. Tubes were centrifuged at 200 g at room temp for 20 min. 45 ml of the wash was carefully removed by pipet. The pellet was gradually suspended in the remaining 5 ml of media and the cells were transferred to a 15 ml conical tube. The tube was rinsed with 5 ml of media and the rinse was slowly added dropwise to the cell suspension in 15 ml conical tubes, gently swirling each addition of several drops of media. The tube was rinsed a second time with 4 ml of media and the rinse was slowly added to the 15 ml conical tube, as above. The tubes were then centrifuged at 200 g for 20 min. 12 ml of wash was carefully removed by pipet.

The pellet was gently resuspended in the remaining 2ml of media and counted.

The cells were allowed to rest for 1 hour at 37° C. and 50% $CO_2$. They were counted a second time and $5\times10^6$ cells+5 ml QBSF®58 media+Cytokine A (70 ul) were placed in each T175 flask. Media and Cytokine A was provided by Poietic Technologies; their composition was unknown to the present inventors. Considering the state of the art, it is very likely that the media contained FCS, since if it were serum-free, this would have been a remarkable advance that Poietic Technologies would surely have advertised. These cells were used as a positive control since Poetic Technologies advertises this system as a source of dendritic cells.

The cells were placed in an incubator at 37° C., 5% $CO_2$. Cultures were fed 3 days post-thaw (day 10) by adding 25 ml QBSF®58 media+25 ul Cytokine B (again, provided by Poietic Tech., composition unknown. The cells were harvested day 7 post thaw (day 14) by agitating the flask, then removing and saving the cell suspension. Adherent cells were treated with 5mM EDTA for 10 min at 37° C. Diluted 2X with 1% HA/PBS to buffer the EDTA.

Cells were centrifuged at 400 g for 10 min. and resuspended in RPMI/10%cFCS, used for phenotyping, cytospin/morphological identification, and MLR.

Phenotyping of Cultured Cells

Staining of Cells: Approximately $1\times10^6$ cells were transferred into multiple 12×75 mm polypropylene tubes. One ml of PAB was added to each tube, and cells were collected by centrifugation for 3 minutes at room temperature at HIGH setting (1,000×g) using a SERO-FUGE II. The supernatants were poured off, the excess liquid was blotted on absorbent paper and the tubes were gently vortexed to loosen the cell pellets. The cells were stained by adding conjugated and pure antibodies as follows (the choice of mAb varied with each experiment):

| Pure | FITC conjugated Isotype IgG | PE conjugated Isotype IgG |
|---|---|---|
|  | Goat anti-mouse Ig (GAM)* | GAM |
|  | GAM | CD34 |
| CD35 | GAM |  |
|  |  | CD1a |
| CD1a | GAM |  |
|  | CD14 | HLA-DR |
| CD80 |  | GAM |
|  | CD80 |  |
|  |  | CD86 |

*GAM used was a F(ab)'$_2$ (Immunotech).

Viability was determined and FACS analysis was performed as described above in Example 1.

Cytospin slides were prepared as described in Example 1. Slides were split into two groups per culture condition, 1 slide intended for Wright-Geimsa staining, with the remaining slides fixed in acetone for 30 seconds and allowed to air dry. Wright-Geimsa staining was done as described in Example 1 above.

Immunocytochemical staining: PBS (phosphate buffered saline) was made by dissolving 5 PBS tablets into 1000 ml millipore water. Cytospin slides were soaked in PBS. Endogenous peroxidase activity was blocked by treating slides with hydrogen peroxide/PBS (2 ml 30% $H_2O_2$+30 ml PBS) for 10 min. Slides were rinsed with PBS one time. Non-specific binding sites were blocked by incubating with normal serum matching source of secondary antibody (i.e. if secondary antibody is biotinylated goat-anti-mouse, used normal goat serum) at room temp. for 15 min. in a humidified environment. Excess serum was shaken from slides and placed 100 ul of primary antibody on slide, making sure cells are covered with liquid and incubated in humidified environment, room temp, for one hour. Negative control slides were incubated with normal serum for this hour. Slides were rinsed 3 times with PBS. Slides were incubated with biotinylated antibody reactive against the primary antibody (i.e. if primary antibody is mouse-anti-human, use a biotinylated goat-anti-mouse antibody) for 1 hour in humidity. Slides were rinsed 3 times with PBS. Slides were incubated with streptavidin-peroxidase, 2 drops/slide, for 30 min. in humidity. Slides were rinsed 3 times with PBS.

Chromagen solution was made with 5 ml millipore water+2 drops of chromagen buffer+1 drop of concentrated chromagen+1 drop of substrate, and 4–5 drops were added to each slide. Slides were incubated for 2–10 min., until the cells showed positive red color, then rinsed with distilled water. Slides were counterstained with hematoxylin for about 5 min, or until cell nuclei were stained purple. Cells were rinsed with tap water and allowed to air dry. Slides were covered with crystal mount and oven dried at 80 degrees for 15 min. Slides were allowed to cool, then coversliped with mounting medium.

Mixed Lymphocyte Reactions (MLR) were performed as described in Example 1 above.

RESULTS

CD34+ Cell-derived Dendritic Cells, Serum-containing media in a Flask vs. Serum-free media in a PL2417 Container.

Tables 7 and 8 show the average phenotype, morphology, and MLR values of 3 experiments designed to test the feasibility of culture deriving dendritic cells from thawed CD34+ cells, using serum-free conditions and PL2417 containers. Each experiment consisted of two cultures at $1\times10^5$ cells/ml in 100 ml media+100 U/ml GM-CSF+100U/ml TNF-α. As a positive control, culture 1 was grown in RPMI supplemented with 10% FCS, a condition typically cited in literature as conducive to dendritic cell growth. Culture 2 contained serum-free X-VIVO 15™ in PL2417 containers. In one case, 1% HA was used as a supplement in the serum-free culture, without significant improvement in cell growth, phenotype or stimulatory capacity (data not shown). Phenotypic analysis over the 14 day culture shows the following trends in surface expression: decreased expression of CD34, expected as the cells differentiate as a result of culture; increased CD80 expression in both cultures, again higher in the serum-free culture; and an increase in the CD86 expression that seemed equivalent in both cultures. CD1a expression showed slight fluctuations, but no consistent increase.

Cells displaying dendritic cell morphology increased to an average of 25% for RPMI culture and 32% for serum-free by day 14, as evidenced by Wright-Geimsa staining. Dendritic cells were identified by cytoplasmic processes or "veils" that extend from the surface of the cells. The S100 antibody was used in the immunohistochemical staining of the cells of cytospins and seems to correlate best with the CD80 phenotyping. MLR's performed showed a moderate proliferative response when stimulated with 10,000 cells from dendritic cell enriched cultures.

TABLE 7

| Day | Culture Condition | Viability | Phenotype | | | | |
|---|---|---|---|---|---|---|---|
|  |  |  | 34+ | 1a+ | 14-/DR+ | 80+ | 86+ |
| 0 |  | 98.53% | 88.99% | 0.06% | 89.25% | 3.53% | 3.40% |
| 7 | RPMI/10%FCS | 93.29% | 11.11% | 2.30% | 54.31% | 27.16% | 18.88% |
|  | X-VIVO 15 | 86.48% | 12.30% | 0.81% | 89.07% | 34.85% | 22.76% |
| 14 | RPMI/10%FCS | 89.69% | 0.34% | 0.43% | 39.59% | 32.86% | 17.43% |
|  | X-VIVO 15 | 61.12% | 1.20% | 1.36% | 77.67% | 41.01% | 15.63% |

TABLE 8

| Day | Culture Condition | Morphology Dc | Morphology Non-DC | Antibody: S100 + | Antibody: S100 − | MLR: CPM 10,000 Stim. | MLR: CPM 1,000 stim. | MLR: CPM 100 stim. | MLR: CPM 10 stim. |
|---|---|---|---|---|---|---|---|---|---|
| 0 |  | 0 | 100 | 12 | 88 | 17,385 | 11,910 | 9,400 | 10,455 |
| 7 | RPMI/10%FCS | 14.66 | 85.34 | 48 | 52 | 39,534 | 10,788 | 4,058 | 2,535 |
|  | X-VIVO15 | 14 | 86 | 47 | 53 | 37,054 | 7,137 | 2,479 | 1,916 |
| 14 | RPMI/10%FCS | 25 | 75 | 36 | 64 | 30,437 | 10,274 | 5,645 | 6,015 |
|  | X-VIVO 15 | 32 | 68 | 46 | 34 | 37,273 | 5,947 | 2,398 | 1,695 |

Tables 9 and 10 summarize preliminary data from one experiment using conditions similar to those above. Fresh CD34+ cells were utilized at a higher concentration, $3 \times 10^5$ cells/ml, under the same media/flask/cytokine conditions. resulted in a clear population of CD1a positive cells. These data are again reinforced by the morphologic and MLR data. Interestingly, cells derived from the serum-free culture seem to have a much greater stimulatory capacity at day 7.

TABLE 9

| Day | Culture Condition | Viability | Phenotype 34+ | CD4+/CD− | CD80+ | CD86+ | CD1a+ |
|---|---|---|---|---|---|---|---|
| 0 |  | 95.70% | 58.13% | 1.47% | 13.05% | 7.61% | 8.56% |
| 7 | RPMI/10%FCS | 94.36% | 9.61% | 81.10% | 13.84% | 4.86% | 5.83% |
|  | X-VIVO 15 | 94.82% | 33.80% | 42.45% | 27.71% | 21.72% | 7.75% |
| 14 | RPMI/10%FCS | 99.31% | 0.00% | 61.10% | 49.90% | 49.24% | 23.54% |
|  | X-VIVO 15 | 86.07% | 1.05% | 52.16% | 46.50% | 17.63% | 11.70% |

TABLE 10

| Day | Culture Condition | Morphology DC | Morphology Non-DC | MLR: CPM 10,000 Stim. | MLR: CPM 1,000 Stim. | MLR: CPM 100 Stim. | MLR: CPM 10 Stim. |
|---|---|---|---|---|---|---|---|
| 0 |  | 0 | 100 | ND | ND | ND | ND |
| 7 | RPM 1/10% FCS | 58 | 42 | 28,835 | 8,181 | 4,740 | 3,423 |
|  | X-VIVO 15 | 66 | 34 | 72,830 | 30,738 | 7,675 | 3,135 |
| 7 | RPM 1/10% FCS | 27 | 73 | 27,964 | 2,275 | 1,780 | 1,281 |
|  | S-VIVO 15 | 43 | 57 | 38,867 | 15,571 | 5,241 | 711 |

Phenotyping was changed to exclude CD14/HLA-DR, and included CD4/CD3. Dendritic cells are reputed to be CD3 negative, but CD4 positive. The CD1a stain was also changed to a new PE-conjugated antibody that made a more easily-resolved population because of brighter fluorescence. This culture follows similar trends as the previous, with the addition that a high percentage of the populations were CD3−/CD4+. In addition, the new antibody to CD1a resulted in a clear population of CD1a positive cells. These data are again reinforced by the morphologic and MLR data. Interestingly, cells derived from the serum-free culture seem to have a much greater stimulatory capacity at day 7.

Cytospin slides from this culture were also stained immunohistochemically on day 14 using a panel of 5 antibodies chosen on the basis of positive staining of a commercially available source of dendritic cells (under results, Dendritic cells derived from Poietic Technologies). Table 11 summarizes the percentages positive of each antibody. The X-VIVO 15™ condition has more positive cells, correlating with the greater stimulatory capacity indicated above.

TABLE 11

| Day | Culture | S100 @ 1:100 | | CD86 @ 1:50 | | CD80 @ 1:20 | | CD1a @ 1:10 | |
|---|---|---|---|---|---|---|---|---|---|
| | | + | − | + | − | + | − | + | − |
| 0 | | 8 | 92 | NA | NA | NA | NA | NA | NA |
| 7 | RPMI/10%FCS | 23 | 77 | NA | NA | NA | NA | NA | NA |
| | X-VIVO 15 | 27 | 73 | NA | NA | NA | NA | NA | NA |
| 14 | RPMI/10%FCS | 26 | 74 | 27 | 73 | 0 | 100 | 0 | 100 |
| | X-VIVO 15 | 41 | 59 | 40 | 60 | 14 | 86 | 8 | 92 |

CD34-derived Dendritic Cells: Media Comparison in Plates. The purpose of these two experiments was to determine the effects, if any, of different media on dendritic cell differentiation. Fresh apheresis product CD34+ cells were set up in 20 ml cultures in 4 well plates using 100 U/ml GM-CSF and TNF-α. The four media used were RPMI/0%FCS, X-VIVO 15™, X-VIVO 15 ™/1% HA, and PROGENitor™-34 media. As shown in Tables 12 and 13, the average viabilities were consistently high, the lowest being PROGENitorm™-34. The percentages of phenotypic expression followed a similar pattern as previous experiments, with decreased CD34 expression over time due to differentiation of the cells. CD80 expression increased by Day 14 in all but the PROGENitorm™-34 media. CD86 expression increased substantially at Day 14 in cultures in X-VIVO 15™ and RPMI/10%FCS, and to a lesser degree in X-VIVO 15™/1HA and PROGENitor™-34 . Again, there was a high percentage by day 7 of CD4+/CD3−cells, except in the PROGENitor™-34 media. There was no upregulation of CD1a expression. Two other CD1a antibodies were also evaluated in these experiments from alternate sources Biosource and Serotec (data not shown), but there was little or no staining.

These cultures showed a good stimulatory capacity in the MLR at day 14 across all the media, with the RPMI/10%actually being lowest, suggesting that dendritic cells are present in all of the cultures to some extent. It is possible that this greater stimulation correlates with the higher CD80 expression. Immunohistochemically, the average numbers of cells positive for S100 are much higher in the X-VIVO 15™ cultures at day 14, providing the best correlation thus far with the greater stimulatory capacity of those two cultures.

Tables 12 and 13. Evaluation of Dendritic Cell Culture in Various Media

TABLE 12

| | Culture | | Phenotype | | | | |
|---|---|---|---|---|---|---|---|
| Day | Condition | Viability | 34'0 | CD4+/CD3− | CD80+ | CD86+ | CD 1a+ |
| 0 | | 91.53% | 86.46% | 6.38% | 23.56% | 4.16% | 9.18% |
| 7 | RPMI/10%FCS | 87.86% | 22.14% | 64.92% | 10.46% | 1.56% | 2.04% |
| | X-VIVO 15 | 90.53% | 13.14% | 54.64% | 21.13% | 2.79% | 3.61% |
| | X-VIVO 15/1%HA | 74.96% | 22.22% | 38.26% | 14.13% | 8.77% | 0.20% |
| | Progenitor 34 | 66.81% | 19.77% | 41.60% | 11.04% | 2.06% | 0.91% |
| 14 | RPMI/10% FCS | 96.62% | 2.69% | 55.70% | 29.56% | 18.83% | 4.43% |
| | X-VIVO 15 | 91.89% | 2.58% | 65.05% | 41.62% | 15.43% | 3.47% |
| | X-VIVO 15/1%HA | 90.54% | 1.08% | 51.92% | 34.25% | 9.26% | 0.60% |
| | Progenitor 34 | 77.71% | 1.14% | 20.65% | 17.13% | 5.95% | 0.00% |

TABLE 13

| | | | | Antibody: | | MLR: CPM | | | |
|---|---|---|---|---|---|---|---|---|---|
| | | Morphology | | S100 | | 10,000 | 1,000 | 100 | 10 |
| Day | Culture Condition | DC | Non-DC | + | − | Stim. | Stim. | Stim. | Stim. |
| 0 | | 0 | 100 | 7 | 93 | ND | ND | ND | ND |
| 7 | RPMI/10%FCS | 52 | 49 | 23 | 77 | 26,522 | 8,488 | 6,272 | 6,920 |
| | X-VIVO 15 | 59 | 41 | 25 | 75 | 34,203 | 8,671 | 6,792 | 5,607 |
| | X-VIVO15/1%HA | 28 | 72 | 20 | 80 | 25,685 | 8,584 | 4,827 | 4,918 |
| | Progenitor 34 | 37 | 63 | 30 | 70 | 17,430 | 8,584 | 4,827 | 4,918 |
| 14 | RPMI/10%FCS | 54 | 46 | 24 | 76 | 34,291 | 6,673 | 3,488 | 3,613 |
| | X-VIVO 15 | 31* | 69* | 43 | 57 | 63,017 | 21,209 | 5,441 | 4,256 |
| | X-VIVO15/1%HA | 38* | 62* | 46 | 54 | 50,340 | 16,590 | 6,646 | 4,113 |
| | Progenitor 34 | 2i | 78 | 27 | 73 | 53,735 | 22,251 | 5,560 | 3,438 |

*not average of 2 like the other; N = 1 because other slides questionable.

Dendritic Cells Derived from Poietic Technologies:

The source of cells bought from Poietic Technologies is CD34+ cells isolated from bone marrow. Three separate experiments were set up with these cells. The first experiment was to culture the cells as instructed by Poietic Technologies as a positive control for the methods of the invention. The cells received were frozen at day 7 culture, subsequently thawed and cultured in-house for another 7 days, for a total of 14 days. The cells were stained with a panel of fluorescent antibodies, stained for morphology, and set up in an MLR. Phenotype showed an increase in CD80 expression. These day 14 cells also showed increased expression of CD1a.

Morphology data also confirms the presence of dendritic cells in the culture, but not the 90% expected from the advertising of Poietic Technologies. The cultured cells are not very effective at stimulating T-cells, however this may be a reflection of the poor day 7 viabilities, possibly attributed to the 5 mM EDTA treatment to remove the adherent cells from the flask.

TABLE 14

| Day | Culture Condition | Viability | Phenotype | | | | |
|---|---|---|---|---|---|---|---|
| | | | 34+ | CD80+ | CD86+ | CD1a+ | CD14 |
| 0 | Day 7 progenitor | 98.47% | 11.82% | 17.32% | 16.54% | 5.72% | 11.14% |
| 7 | Day 14 progenitor | 19.57% | 6.83% | 31.27% | 14.21% | 12.08% | 0.14% |

TABLE 15

| Day (Cont'd) | HLA-DR |
|---|---|
| 0 | 74.65% |
| 7 | 65.54% |

TABLE 16

| | | Morphology | | MLR: CPM | | | |
|---|---|---|---|---|---|---|---|
| | | | | 10,000 | 1,000 | 100 | 0 |
| DAY | Culture Condition | DC | Non-DC | Stim. | Stim. | Stim. | Stim. |
| 0 | Day 7 progenitor | 0 | 100 | 104 | 753 | 540 | 122 |
| 7 | Day 14 progenitor | 16 | 84 | 2,450 | 10,343 | 1,538 | 1,259 |

Because Wright-Geimsa staining resulted in very clear morphological identification of dendritic cells, two additional cultures, DC-1 and DC-2, were set up to be used as controls to test a variety of antibodies and for immunohistochemical slides. Due to the large number of available fluorescent antibodies and conflicting reports on the phenotypic expression of molecules on the surface of dendritic cells, to date there has been no antibody or series of antibodies used as a definitive phenotypic test for dendritic cells. Cells were stained at Day 14 with a panel of antibodies from different companies in order to define a set of antibodies that could be used as reliable markers for cultured dendritic cells. Dendritic cells were defined based on autofluorescence patterns and light scatter. A gate was drawn to include these autofluorescent cells which fell in the granular region of light scatter, then dead cells were excluded using propidium iodide. The antibodies and the percentages of cells that were found positive for that marker follow in Table 17.

TABLE 17

Evaluation of Dendritic Cell Antibodies via Staining of Poietic Technologies Cells

| | Day 14: DC-1 | | Day 14: DC-2 | |
|---|---|---|---|---|
| | Dendritic Cells | Non-dendritic Cells | Dendritic Cells | Non-dendritic Cells |
| 1. CD1a-PE: Coulter | 27.09% | 5.14% | 43.58% | 6.59% |
| 2. CD86-PE: Ancell | 63.18% | 7.61% | 65.40% | 9.85% |
| 3. CD3−/CD4+: BD | 66.46% | 48.11% | ND | ND |

TABLE 17-continued

Evaluation of Dendritic Cell Antibodies via Staining of Poietic Technologies Cells

| | Day 14: DC-1 | | Day 14: DC-2 | |
|---|---|---|---|---|
| | Dendritic Cells | Non-dendritic Cells | Dendritic Cells | Non-dendritic Cells |
| 4. CD80 unconjugated: Immunotech/ 2nd GAM-FITC: BD | 24.15% | 2.88% | ND | ND |

TABLE 17-continued

Evaluation of Dendritic Cell Antibodies via Staining of Poietic Technologies Cells

| | Day 14: DC-1 | | Day 14: DC-2 | |
|---|---|---|---|---|
| | Dendritic Cells | Non-dendritic Cells | Dendritic Cells | Non-dendritic Cells |
| 5. CD35 unconjugated: DAko/2nd GAM-FITC: BD | 12.71% | 4.26% | ND | ND |
| 6. CD1a unconjugated: BD/2nd GAM-FITC: BD | ND | ND | 8.16% | 1.59% |
| 7. CD80-PE: BD | ND | ND | 89.06% | 14.00% |

Cytospin slides were also prepared from the two cultures reported above, including both Wright-Geimsa and acetone-fixed for immunohistochemical analysis. Six different antibodies were chosen based on literature citations and results of phenotypic analysis above: CD86, S100, CD35, CD80 (Immunotech), CD80-PE (BD), and CD1a (Coulter). Various dilutions of antibodies were used in the assay, from 1:10 to 1:1000, to determine the optimal titration for immunohistochemical staining, as shown in Tables 18 and 19. This determination was based on intensity of staining of individual positive cells and the lack of background, or non-specific staining. CD35 showed approximately 4 positive cells (data not shown) and CD80-PE showed none, and was not used in subsequent staining.

Tables 18 and 19. Evaluation of Dendritic Cells from Poietic Tecnologies: Immunohistochemistry

TABLE 18

| | Wright-Geimsa | | | Antibody | | | | |
|---|---|---|---|---|---|---|---|---|
| | | | | S100 @ 1:100 | | CD86 @ 1:50 | | CD80 @ 1:20 |
| Culture | DC | NR* | Non-DC | + | − | + | − | + | − |
| DC-1 | 49 | 10 | 41 | 56 | 44 | 33 | 67 | NA | NA |
| DC-2 | 50 | 10 | 40 | 54 | 46 | 41 | 59 | 14 | 86 |

*Not Recognized

TABLE 19

| | CD 1a @ 1:100 | |
|---|---|---|
| Culture (cont'd) | + | − |
| DC-1 | NA | NA |
| DC-2 | 36 | 64 |

The purpose of this series of experiments was to determine the feasibility of culture deriving dendritic cells utilizing selected CD34+ cells in serum-free media in PL2417 containers. To this end, a number of different media/culture conditions were evaluated to determine possible effects on dendritic cell differentiation, as evidenced by phenotype, morphology, immunohistochemistry, and MLR data. Efforts were made to correlate expression of some of the commonly cited surface molecules with the positive identification by morphology (Wright-Geimsa staining), immunohistochemistry and stimulatory capacity in MLR. CD1a is commonly cited as a dendritic cell marker, yet expression was not always consistent in these cultures. The most consistent results are increased expression of CD80 and CD86, T-cell costimulatory molecules whose presence on the cell surface is consistent with the role of the dendritic cell as a professional antigen presenting cell.

Despite the lack of definitive phenotypic staining, the morphological, immunohistochemical, and MLR data were more consistent throughout the experiments. Morphologically, dendritic cells have been identified by the presence of cytoplasmic processes or "veils" that extend from the surface of the cells, observed in the cytospins. Although the counts/min, varied in individual experiments, MLR data show consistent stimulation at the 10,000 stimulators./well condition. Proliferation induced by those cells cultured in X-VIVO 15™ was always at least equivalent to that induced by control cells cultured in 10% serum. In fact, none of the cultures failed to induce proliferation at the 10,000 cells/well condition, supporting the idea that all of the cultures were successful in growing dendritic cells to some extent. Of particular interest, the preliminary data comparing fresh cells in serum vs. PL2417/serum-free shows a noticeable difference in stimulatory capacity, especially at the 1,000 stimulators/well condition (approx. 8,000 vs. 31,000 on day 7, and 2,000 vs. 15,000 on day 14). This is a good verification of the presence of dendritic cells, which are the most efficient stimulators at low concentrations.

Finally, to address issues of variable staining and morphology, Poietic Technologies cells were used as a positive control to test various antibodies for flow cytometric analysis and immunohistochemistry. Based on the panel of flow cytometry antibodies screened, the best correlation of positive staining on dendritic cells and minimal reactivity to non-dendritic cells is with the following antibodies: CD1a-PE, Coulter; CD86-PE, Ancell; and CD80-PE, BD.

In a similar effort, 100 slides from the second Poietic Technologies culture were fixed in acetone and used for immunohistochemistry. S100 diluted 1:100, CD86 diluted 1:50, CD80 at 1:20, CD83 at 1:100, and CD1a at 1:10, were chosen as optimal for determination of dendritic cells immunohistochemically. After optimization, S100 was chosen to stain all slides created from the experiments reported above. Applying this technique yielded further verification of data reported by morphological and stimulatory capacity.

While phenotypic staining results are variable and not yet definitive in the identification of dendritic cells, the combination of morphology, functional data via stimulatory capacity, and immunohistochemistry support the conclusion that dendritic cells can be culture derived from CD34+ cells cultured serum-free in culture containers having a polystyrene growing surface.

EXAMPLE 3

Co-culturing and Immunostaining of Tetanus Toxin Antigen-pulsed DC.

Materials: All materials were as described above, and in addition:
Tetanus Toxin C fragment, recombinant, Boehringer Mannheim, #1348 655, Indianapolis, Ind.
Anti-Tetanus Toxin C fragment, Boehringer Mannheim, #1131 621, Indianapolis, Ind.

Methods:
CD34+ cell selection was performed using Isolex®, per Manual instructions.

Cell sources:
1) DC culture derived from CD34+ cells/T-cells from non-targeted (non-CD34-selected) fraction. Fresh CD34+ cells and the non-CD34-selected fraction were counted on Coulter counter in 10 ml cetrimide+20 ul of sample cells. Viability and CD34+ percentages were assessed prior to setting up the experiment via PI exclusion of dead cells, anti-CD34 PE staining, and acquisition on FACSort.

To culture-derive DC, the appropriate volume of 34+ cell suspension was added to make a final concentration of $3\times10^5$ cells/ml in 100 ml of X-VIVO 15™, plus 100U/ml GM-CSF and 100 U/ml TNF-$\alpha$, and cultured in the PL2417 "window" container.

To culture-derive T-cells, the appropriate volume of non-CD34-selected cell suspension was added to make a concentration of $5\times10^5$ cells/ml in 300 ml of X-VIVO 15™, plus 50 ng/ml OKT-3 and 100 U/ml IL-2, and cultured in the PL2417 container. The PL2417 container was filled using a 250 ml conical tube, pouring the appropriate cell suspension into a 60 ml syringe barrel attached as a funnel to an injection port of the PL2417 container via a needle.

At day 7, DC/T-cell co-cultures were set up by adding the autologous T-cells to the PL2417 "window" container at a T-cells:DC ration of 10:1. Cytospin slides were made after 7 days of co-culture.

Phenotyping and morphological analysis were performed as described in Examples 1 and 2 above.

Results are shown in Tables 20–25 below:

TABLE 20

| Day | condition | cells/ml | vol. | sample vol. | viability | total cells | total cells cont. | PI |
|---|---|---|---|---|---|---|---|---|
| 0 |   | 3.00E + 05 | 100 | 0 | 86.99% | 2.61E + 07 | 2.61E + 07 | 1.00 |
| 8 | 1 | 3.03E + 05 | 100 | 100 | 97.19% | 2.94E + 07 | 0.00E + 00 | 1.13 |

TABLE 21

Percent of cells in culture.

| Day | con-dition | Phenotype | | | | | Morphology | | S100 | | |
|---|---|---|---|---|---|---|---|---|---|---|---|
|   |   | CD1a-PE | CD14-PE | CD34-PE | CD80-PE | CD86-PE | DC | non-DC | S100 neg | S100 dim | S100 brite |
| 0 |   | 0.00% | 2.29% | 89.32% | 0.00% | 0.66% | 0.00% | 100.00% | NA | NA | NA |
| 8 | 1 | 11.99% | 13.25% | 29.04% | 19.87% | 47.45% | 30.00% | 70.00% | 21.00% | 53.00% | 26.00% |

TABLE 22

Total cell numbers.

| Day | con-dition | Phenotype | | | | | Morphology | |
|---|---|---|---|---|---|---|---|---|
|   |   | CD1a-PE | CD14-PE | CD34-PE | CD50-PE | CD80-PE | DC | non-DC |
| 0 |   | 0.00E + 00 | 5.98E + 05 | 2.33E + 07 | 0.00E + 00 | 1.72E + 05 | 0.00E + 00 | 2.61E + 07 |
| 8 | 1 | 3.53E + 06 | 3.91E + 06 | 8.55E + 06 | 5.85E + 06 | 1.40E + 07 | 8.83E + 06 | 2.06E + 07 |

| Day | con-dition | S100 | | |
|---|---|---|---|---|
|   |   | S100 neg | S100 dim | S100 brite |
| 0 |   | 0.00E + 00 | 0.00E + 00 | 0.00E + 00 |
| 8 | 1 | 6.18E + 06 | 1.56E + 07 | 7.66E + 06 |

TABLE 23

| Day | con-dition | cells/ml | vol. | sample vol. | viability | total cells | total cells cont. |
|---|---|---|---|---|---|---|---|
| 0 |   | 5.00E + 05 | 300 | 0 | 100.00% | 1.50E + 08 | 1.50 + 08 |
| 4 | 1 | 1.72E + 05 | 300 | 25 | 88.40% | 4.57E + 07 | 4.19E + 07 |
| 6 | 1 | 1.13E + 06 | 300 | 25 | 97.31% | 3.31E + 08 | 3.03E + 08 |

TABLE 24

| Day | condition | CD3 | CD3/CD4 | CD3/CD8 | CD3/CD25 | CD14 | CD56 |
|---|---|---|---|---|---|---|---|
| 0 |   | 8.56% | 7.28% | 1.61% | 0.04% | 59.44% | 2.61% |
| 4 | 1 | 80.40% | 65.06% | 37.51% | 93.67% | 0.44% | 1.17% |
| 6 | 1 | 97.66% | 59.39% | 58.72% | 98.23% | 0.00% | 1.69% |

TABLE 25

| Day | condition | CD3 | CD3/CD4 | CD3/CD8 | CD3/CD25 | CD14 | CD56 |
|---|---|---|---|---|---|---|---|
| 0 |   | 1.28E + 07 | 1.09E + 07 | 2.42E + 06 | 6.00E + 04 | 8.92E + 07 | 3.92E + 06 |
| 4 | 1 | 3.67E + 07 | 2.97E + 07 | 1.71E + 07 | 4.28E + 07 | 2.01 + _05 | 5.34E + 05 |
| 6 | 1 | 3.52E + 08 | 2.14E08 | 2.12E + 08 | 3.54E + 08 | 0.00E + 00 | 6.10E + 06 |

2) DC and T-cells cultured from MNC:

T-cells were isolated via sheep red blood cell rosetting as follows. Sheep red blood cells were prepared and used to erythrocyte rosette T-cells as described in *Current Protocols in Immunology*, John Wiley and Sons Inc., 1995. Vol. 2, 7.2.1–7.2.4. The Ficoll interface (non-T-cell-MNC) was retained as starting source for culture-deriving dendritic cells. These were set up in 20 ml cultures, plate/RPMI/10% FCS, and 2417container/X-VIVO 15™ at a concentration of $3\times10^5$ cells/ml, stimulated with 100 U/ml GM-CSF and 1000 U/m IL-4.

T-cells from the rosetting step were set up in 40 ml X-VIVO 15™m in 2417 container at a concentration of $5\times10^5$ cells/ml, stimulated with 5 ong/ml OKT-3 and 100 U/ml IL-2.

On Day 7, each dendritic cell-enriched culture was split 3 ways and stimulated with different concentrations of Tetanus Toxin C fragment (TTC), 100 ug/ml, 10 ug/ml and 1 ug/ml for overnight.

Cytospin slides were made of these pulsed dendritic cells for later immunohistochemical examination, then autologous T-cells from the above described culture were added at a T-cell:DC ratio of 5:1. Co-cultures were maintained for 21 days, with cytospin slides made at days 7, 14, and 21. Cytospin slides were prepared and Wright-Giemsa stained as described in Example 1 above.

Phenotyping and morphological analysis were performed as described in Examples 1 and 2 above.

Results are shown in Tables 26–32 below:

TABLE 26

| Day | condition | cells/ml | vol. | sample vol. | viability | total cells | total cells cont. | PI | Cumm. PI |
|---|---|---|---|---|---|---|---|---|---|
| 0 |   | 1.00E + 05 | 20 | 0 | 98.92% | 1.98E + 06 | 1.98E + 06 | 1.00 |   |
| 8 | 1 | 6.58E + 05 | 20 | 5 | 90.89% | 1.20E + 07 | 8.97E + 06 | 6.05 |   |
|   | 2 | 5.10E + 05 | 20 | 5 | 94.90% | 9.68E + 06 | 7.26E + 06 | 4.89 |   |
|   | 3 | 3.99E + 05 | 20 | 5 | 87.35% | 6.97E + 06 | 5.23E + 06 | 3.52 |   |
|   | 4 | 4.08E + 05 | 20 | 5 | 83.60% | 6.82E + 06 | 5.12E + 06 | 3.45 |   |
| 14 | 1 | 5.00E + 04 | 20 | 20 | 93.30% | 9.33E + 05 | 0.00E + 00 | 0.10 | 0.63 |
|   | 2 | 5.02E + 04 | 20 | 20 | 83.09% | 8.34E + 05 | 0.00E + 00 | 0.11 | 0.56 |
|   | 3 | 6.78E + 04 | 20 | 20 | 91.85% | 1.25E + 06 | 0.00E + 00 | 0.24 | 0.84 |
|   | 4 | 4.76E + 04 | 20 | 20 | 88.01% | 8.38E + 05 | 0.00E + 00 | 0.16 | 0.56 |

TABLE 27

| Day | condition | Phenotype | | | | | Morphology | |
|---|---|---|---|---|---|---|---|---|
|   |   | CD1a-PE | CD14-PE | CD34-PE | CD80-PE | CD86-PE | DC | non-DC |
| 0 |   | 0.00% | 47.30% | 0.32% | 0.00% | 7.32% | 0.00% | 100.00% |
| 8 | 1 | 36.43% | 0.30% | 0.30% | 31.79% | 49.42% | 46.00% | 54.00% |
|   | 2 | 16.96% | 0.41% | 0.00% | 35.90% | 50.41% | 18.00% | 82.00% |
|   | 3 | 13.24% | 0.18% | 0.00% | 16.41% | 47.87% | 28.00% | 73.00% |
|   | 4 | 8.77% | 0.00% | 0.39% | 15.62% | 45.19% | 32.00% | 68.00% |
| 14 | 1 | 17.22% | 0.00% | NA | 26.87% | 46.58% | 22.00% | 78.00% |
|   | 2 | 7.01% | 0.00% | NA | 18.13% | 56.52% | 20.00% | 80.00% |
|   | 3 | 9.12% | 0.00% | NA | 6.86% | 59.95% | 16.00% | 84.00% |
|   | 4 | 1.70% | 0.00% | NA | 7.17% | 73.67% | 21.00% | 79.00% |

TABLE 28

| Day | con-dition | Phenotype | | | | | Morphology | |
|---|---|---|---|---|---|---|---|---|
| | | CD1a-PE | CD14-PE | CD34-PE | CD80-PE | CD86-PE | DC | non-DC |
| 0 | | 0.00E + 00 | 9.36E + 05 | 6.33E + 03 | 0.00E + 00 | 1.45E + 05 | 0.00E + 00 | 1.98E + 06 |
| 8 | 1 | 4.36E + 06 | 0.00E + 00 | 3.59E + 04 | 3.80E + 06 | 5.91E + 06 | 5.50E + 06 | 6.46E + 06 |
| | 2 | 1.64E + 06 | 3.97E + 04 | 0.00E + 00 | 3.48E + 06 | 4.88E + 0E | 1.74E + 06 | 7.94E + 06 |
| | 3 | 9.23E + 05 | 1.25E + 04 | 0.00E + 00 | 1.14E + 06 | 3.34E + 06 | 1.95E + 06 | 5.09E + 06 |
| | 4 | 5.98E + 05 | 0.00E + 00 | 2.66E + 04 | 1.07E + 06 | 3.08E + 06 | 2.18E + 06 | 4.64E + 06 |
| 14 | 1 | 2.14E + 05 | 0.00E + 00 | 0.00E + 00 | 3.34E + 05 | 5.97E + 05 | 2.74E + 05 | 9.70E + 05 |
| | 2 | 7.80E + 04 | 0.00E + 00 | 0.00E + 00 | 2.02E + 05 | 6.29E + 05 | 2.22E + 05 | 8.90E + 05 |
| | 3 | 1.51E + 05 | 0.00E + 00 | 0.00E + 00 | 1.14E + 05 | 9.96E + 05 | 2.66E + 05 | 1.39E + 06 |
| | 4 | 1.90E + 04 | 0.00E + 00 | 0.00E + 00 | 8.01E + 04 | 8.23E + 05 | 2.35E + 05 | 8.83E + 05 |

TABLE 29

| Day | con-dition | cells/ml | vol. | sample vol. | viabilty | total cells | total cells cont. | PI | Cumm. PI |
|---|---|---|---|---|---|---|---|---|---|
| 0 | T-cells | 5.00E + 05 | 20 | 0 | 90.95% | 9.10E + 06 | 9.10E + 06 | 1.00 | |
| 7 | 1 | 3.33E + 06 | 20 | 5 | 93.37% | 6.22E + 07 | 4.66E + 07 | 6.84 | |
| 14 | 1 | 1.46E + 06 | 50 | 50 | 91.67% | 6.78E + 07 | 0.00E + 00 | 1.45 | 9.94 |

TABLE 30

| Day | Condition | CD3-FITC | CD25-PE | CD4-PE | CD8-PE | CD14-FITC | CD56-PE |
|---|---|---|---|---|---|---|---|
| 0 | | 86.12% | 0.12% | 49.15% | 28.69% | 3.93% | 6.69% |
| 7 | 1 | 93.45% | 73.81% | 21.39% | 80.53% | 0.00% | 11.75% |
| 14 | 1 | 96.19% | 13.54% | 7.53% | 86.28% | 0.00% | 33.42% |

TABLE 31

| Day | condition | CD3-FITC | CD25-PE | CD4-PE | CD8-PE | CD14-FITC | CD56-PE |
|---|---|---|---|---|---|---|---|
| 0 | | 7.83E + 06 | 1.09E + 04 | 4.47E + 06 | 2.61E + 06 | 3.57E + 05 | 6.08E + 05 |
| 7 | 1 | 5.81E + 07 | 4.59E + 07 | 1.33E + 07 | 5.01E + 07 | 0.00E + 00 | 7.31E + 06 |
| 14 | 1 | 8.70E + 07 | 1.22E + 07 | 6.81E + 06 | 7.80E + 07 | 0.00E + 00 | 3.02E + 07 |

TABLE 32

| Day | Condition | cells/ml | vol. | sample vol. | viability | total cells | total cells cont. | PI | Cumm. PI |
|---|---|---|---|---|---|---|---|---|---|
| 8 | DC + T-cells | 5.50E + 05 | 15 | 0 | 90.95% | 7.50E + 06 | 7.50E + 06 | 1.00 | |
| 14 | 4 | 1.92E + 06 | 15 | 15 | 93.37% | 2.69E + 07 | 0.00E + 00 | 3.58 | |

Immunocytochemical staining: PBS (phosphate buffered saline) was made by dissolving 5 PBS tablets into 1000 ml millipore water. Cytospin slides were soaked in PBS. Endogenous peroxidase activity was blocked by treating slides with hydrogen peroxide/PBS (2 ml 30% $H_2O_2$+30 ml PBS) for 10 min. Slides were rinsed with PBS one time. Non-specific binding sites were blocked by incubating with normal serum matching source of secondary antibody (i.e. if secondary antibody is biotinylated goat-anti-mouse, used normal goat serum) at room temp. for 15 min. in a humidified environment. Excess serum was shaken from slides and 100 ul of primary antibody was placed on the slide, making sure cells are covered with liquid and incubated in humidified environment, room temp, for one hour. Negative control slide was incubated with normal serum for this hour. Slides were rinsed 3 times with PBS. Slides were incubated with biotinylated antibody reactive against the primary antibody (i.e. if primary antibody is mouse-anti-human, used a biotinylated goat-anti-mouse antibody) for 1 hour in humidity. Slides were rinsed 3 times with PBS. Slides were incubated with streptavidin-peroxidase, 2 drops/slide, for 30 min. in humidity. Slides were rinsed 3 times with PBS. Chromagen solution was made by mixing 5ml millipore water+2 drops of chromagen buffer +1 drop of concentrated chromagen+1 drop of substrate, and 4–5 drops were added to each slide. Slides were incubated for 2–10 min., until cells showed positive red color, then rinsed with distilled water. Slides were counter-stained with hematoxylin for about 5 min, or until cell nuclei were stained purple. Slides were rinsed with tap water and let air dry. Slides were rinsed with crystal mount and oven dried at 80 degrees for 15 min, cooled, and coversliped with mounting medium.

RESULTS: Cells which were prominently stained for tetanus toxoid antigen also displayed characteristic DC processes (see FIG. 9). Cells with lymphocyte morphology appeared unstained by the tetanus toxoid antigen antibody.

EXAMPLE 4

Culture of DC from Umbilical Cord Blood

CD34+ cells from umbilical cord blood (CB) offer certain advantages over cells obtained from bone marrow or peripheral blood in that the CB CD34+ cells are naive, highly proliferative, and the risk of culturing and reinfusing tumor cells is diminished. For these studies, CB mononuclear cells were obtained from CB samples using a 1.2% hetastarch solution in sodium chloride (HESPAN®, DuPont). CD34+ cells were isolated using the Isolex® magnetic bead CD34 cell selection method described above. The average viability and CD34 purity, post-selection, was 7.19% and 67.50% respectively. Cells were cultured at $3\times10^4$ cells/ml in 6 well plates containing serum-free media (EX-VIVO 15™, BioWhittaker) or serum-free media supplemented with 10% autologous CB plasma (n=2). Cells were fed with 200 U/ml GM-CSF and 50 U/ml TNF-α or with 200 U/ml GM-CSF, 50 U/ml TNF-α, 10 ng/ml SCF, and 50 U/ml IL-3. Cells were counted and analyzed at days 0, 11, and 25 for the presence of DC. DC were identified by their expression of CD1a, CD80, and CD86 by flow cytometric methods, immunohistochemically using an anti-S100 antibody, and morphologically by Wright-Geimsa staining. At day 11, the highest average percent of cells displaying DC characteristics was obtained in cultures containing only GM-CSF and TNF-α with no added autologous plasma. Morphologically, 51% of these cells were DC. Although the highest average amount of proliferation (32 fold) at day 11 was obtained in cultures containing GM-CSF, TNF-α, SCF, and IL-3 with 10% plasma, the average percent of characterized DC was not greatly enhanced and morphologically only 5% of the cells were DC. Viability averaged over 90% throughout the culture period in all culture conditions. Thus, the addition of autologous plasma did not significantly increase the purity of DC and although addition of SCF and IL-3 to the GM-CSF and TNF-α combination did induce greater proliferation, the purity and overall number of characterized DC was not significantly enhanced.

EXAMPLE 5

Producing Clinically useful Numbers of DC and Antigen-specific T-lymphocytes.

Antigen-specific T-lymphocytes can be infused into a patient in order to combat cancer cells, for instance. Alternatively, stimulated T-lymphocytes can be administered as a cancer vaccine to prevent recurrence of a specific cancer for which the patient is known to be at risk. For the first indication, it is estimated that about one billion ($10^9$) antigen-specific T-cells would be sufficient to home to and destroy residual cancer cells. It is expected that the entire culture of cells would contain about 10 billion ($10^{10}$) total cells, of which only about 10t would be antigen-specific T-cells. It is also possible that a lower dose of antigen-specific T-cells might be useful for this indication; as few as 100 million antigen-specific T-cells could be effective. On the other hand, for vaccine use, it is expected that higher numbers of antigen-specific T-cells will be necessary.

In order to produce 100 million antigen-specific T-cells, it is estimated that 10 million T-cells will be seeded in the original co-culture with at least two million DC. When higher numbers of antigen-specific T-cells are required, proportionately higher numbers of DC are required in the co-culture. Thus, in order to produce one billion antigen-apecific T-cells, at least 100 million T-cells will be seeded in the initial co-culture with at least 20 million DC.

Using the methods of the invention, sufficient DC can be culture-derived to produce the required number of antigen-specific T-cells. The PL2417 gas-permeable culture bags used in the above experiments have a growing surface area of $75cm^2$, which is designed for a volume of about 20 ml of culture medium. As demonstrated in the above examples, two million T-cell depleted MNC originally seeded in a 20 ml culture yielded two million DC. Thus, for the lowest estimate of required DC, this small-scale culture is sufficient. When 20 million DC are required, for instance, a total of 20 million MNC can be originally seeded in a total volume of 200 ml of culture medium, which can be contained in five clinical-scale culture bags of $150cm^2$ surface area each. Alternatively, the seeding cell concentration can be increased to $3-5\times10^5$ cells/ml, and the media volumes and culture surface areas adjusted accordingly. The culture bags can be manufactured to higher surface areas, as required for a given clinical need. Antigen-pulsing and addition of the requisite number of T-cells can be carried out aseptically in the originally seeded culture bag(s) once the culture has become enriched for DC. Alternatively, DC cultures can be split aseptically by directing a portion of the culture in the original bag to other aseptically attached bags using sterile connections and tubes. Antigen-pulsing and T-cell co-culture can then be performed aseptically in the split DC cultures.

EXAMPLE 6

Dendritic Cells Culture-derived from Adherent Cells

PBMNC were placed into PL2417 gas-permeable containers and allowed to adhere to the container over a 2 hour incubation period. Non-adherent cells were removed and placed into a separate container. For comparison, PBMNC or MNC were also cultured without preadherence, as described above, in both PL2417 gas-permeable containers and Teflon® cell culture bags.

Adherent cells, non-adherent cells, and bulk MNC were all cultured in X-VIVO 15 serum free media supplemented with 2 mM L-glutamine, 50 ng/ml granulocyte/macrophage-colony stimulating factor (GM-CSF), and 1000 U/ml interleukin-4 (IL-4). Analysis for the presence of DC were performed on days 0 and 7 of the culture period, as described above. These analyses included phenotyping for cell surface markers CD1a, CD14, CD80, and CD86 using flow cytometric techniques, immunohistochemical staining for the S100 protein, morphological identification after Wright-Geimsa staining, and in some cases, functional capacity of cultured cells to induce T cell proliferation in an allogeneic mixed lymphocyte reaction (MLR).

Materials: Teflon® Cell Culture Bags were purchased from American Flouroseal Co., Silverspring, Md. All other materials were as described above.

Methods: Mononuclear cells were prepared from whole blood or apheresis product, as described above. PBMNC cells were cultured in X-VIVO 15™ supplemented with 2 mM L-glutamine. Cultures were initiated at $5\times10^5$ cells/ml in PL2417 gas-permeable containers (20 ml) or Teflon® cell culture bags (30 ml). GM-CSF and IL-4 were added to the cultures at final concentrations of 50 ng/ml and 1000 U/ml, respectively. Addition and subtraction of cells, media, and growth factors to and from PL2417 gas-permeable containers was accomplished by spiking a Sampling Site Coupler into the sample port of the container followed by use of syringes and needles. Addition and subtraction of cells, media, and growth factors to and from Teflon® cell culture bags was accomplished by attaching a syringe (without needle) to the female connectors of the sample ports. Cells were cultured in a 5% $CO_2$, ambient $O_2$, 37° C. humidified incubator for 7 days.

For enrichment and culture of adherent cells, PBMNC were resuspended in culture media (X-VIVO 15™) at $2 \times 10^6$ cells/ml. Cells were placed into PL2417 gas-permeable containers (20 ml) or Teflon® cell culture bags (30 ml) and incubated for 2 hours in a 5% $CO_2$, ambient $O_2$ 37° C. humidified incubator.

Non-adherent cells were removed from the containers and set aside, then containers were rinsed with PBS-CMF. The rinse from each container was then removed and also set aside.

Cells remaining in the containers were adherent cells. These cells were cultured by adding 20 ml of X-VIVO 15™ to the PL2417 containers or 30 ml X-VIVO 15™ to the Teflon® cell culture bags then adding GM-CSF and IL-4 at final concentrations of 50 ng/ml and 1000 U/ml, respectively. For analysis purposes only, duplicate containers were made and adherent cells were removed by adding 20 ml (PL2417) or 30 ml (Teflon®) of 1× trypsin to each container. Containers were placed in a 5% $CO_2$, ambient $O_2$, 37° C. humidified incubator for 5 minutes.

The trypsinized cells were removed and then immediately placed into tubes containing cold culture media.

Containers were rinsed with culture media. This rinse was removed and placed into the tubes containing the cells.

Adherent cells were washed by centrifugation, then resuspended in culture media. Cells were counted using the Coulter Counter.

Non-adherent cells were washed by centrifugation at 400×g for 7 minutes at room temperature, then resuspended to $5 \times 10^5$ cells/ml in X-VIVO 15™. Non-adherent cells were placed into fresh PL2417 gas-permeable containers or fresh Teflon® cell culture bags (depending in which container they originated from) then cultured in the presence of GM-CSF (50 ng/ml) and IL-4 (1000 U/ml) for 7 days in a 5% $CO_2$, ambient $O_2$, 37° C. humidified incubator.

As described above, cells were phenotyped, cytospin slides were prepared and read, and mixed lymphocyte reactions (MLR) were conducted.

RESULTS

At Day 0, all cultures exhibited viabilities that averaged in excess of 99% as determined flow cytometrically with propidium iodide (n=3). By day 7, the average viabilities in all cultures was over 95%. The proliferation index (calculated as the total number of cells at day 7 divided by the total number of cells at day 0) average was the highest in the PL2417 adherent cultures, (Table 33).

TABLE 33

Average Viability, Initiating Cell Number, Total Cells in Culture, and PI.

| Day | Condition | cell/ml | vol. | viability | total cells | PI |
|---|---|---|---|---|---|---|
| 0 | MNC PL2417 | 5.00E + 05 | 20 | 99.39% | 9.94E + 06 | 1.00 |
|   | MNC TEFLON | 5.00E + 05 | 30 | 99.39% | 1.49E + 07 | 1.00 |
|   | Non-Ad. PL2417 | 5.00E + 05 | 20 | 99.28% | 9.93E + 06 | 1.00 |
|   | Adherent PL2417 | 1.17E + 05 | 20 | 99.57% | 2.33E + 06 | 1.00 |
| 7 | MNC PL2417 | 2.32E + 06 | 4 | 97.99% | 7.62E + 06 | 0.77 |
|   | MNC TEFLON | 3.37E + 06 | 4 | 98.09% | 1.07E + 07 | 0.72 |
|   | Non-Ad. PL2417 | 3.20E + 06 | 3.5 | 98.86% | 1.03E + 07 | 1.03 |
|   | Adherent PL2417 | 1.03E + 06 | 4 | 95.00% | 4.43E + 06 | 2.27 |

Table 34 shows the average percent phenotype of cells present in the 4 culture conditions at days 0 and 7. By day 7, the average percent of CD14+ cells decreased in all cultures. Furthermore, the PL2417 adherent culture contained the highest average percent of CD1a+, CD80+, and CD86+ cells. Table 35 shows the average total number of cells in the 4 culture conditions expressing certain phenotypic markers. These total cell numbers were calculated by multiplying the percents in Table 34 by the proliferation index and starting cell numbers from Table 33.

TABLE 34

Average of Percent of Cells in Culture Displaying Phenotype.

| Day | condition | Iso-PE | CD1a-PE | CD14-PE | CD90-PE | CD86-PE |
|---|---|---|---|---|---|---|
| 0 | MNC PL2417 | 0.40% | 3.23% | 20.28% | 0.33% | 10.87% |
|   | MNC TEFLON | 0.40% | 3.23% | 20.28% | 0.33% | 10.87% |
|   | Non-Ad. PL2417 | 0.23% | 0.81% | 14.23% | 0.01% | 6.18% |
|   | Adherent PL2417 | 0.90% | 3.82% | 32.22% | 0.00% | 30.61% |
| 7 | MNC PL2417 | 1.33% | 6.66% | 0.63% | 7.30% | 14.16% |
|   | MNC TEFLON | 1.21% | 6.91% | 0.32% | 8.03% | 12.84% |
|   | Non-Ad. PL2417 | 0.88% | 2.45% | 0.00% | 3.39% | 7.28% |
|   | Adherent PL2417 | 2.11% | 15.96% | 1.47% | 9.00% | 31.11% |

TABLE 35

Average of Total Cells in Culture Displaying Phentotype.

| Day | condition | Iso-PE | CD1a-PE | CD14-PE | CD80-PE | CD86-PE |
|---|---|---|---|---|---|---|
| 0 | MNC PL2417 | 3.95E + 04 | 3.21E + 05 | 2.02E + 06 | 3.32E + 04 | 1.08E + 06 |
|   | MNC TEFLON | 5.92E + 04 | 4.81E + 05 | 3.03E + 06 | 4.98E + 04 | 1.62E + 06 |
|   | Non-Ad. PL2417 | 8.96E + 03 | 2.91E + 04 | 1.54E + 06 | 0.00E + 00 | 3.38E + 05 |
|   | Adherent PL2417 | 3.17E + 04 | 1.64E + 05 | 1.03E + 06 | 0.00E + 00 | 1.02E + 06 |
| 7 | MNC PL2417 | 1.04E + 05 | 4.72E + 05 | 4.18E + 04 | 5.28E + 05 | 1.04E + 06 |
|   | MNC TEFLON | 1.24E.05 | 7.50E + 05 | 3.43E + 04 | 8.69E + 05 | 1.39E + 06 |
|   | Non.Ad PL2417 | 1.06E + 05 | 2.50E + 05 | 0.00E + 00 | 3.59E + 05 | 7.81E + 05 |
|   | Adherent PL2417 | 1.04E + 05 | 9.34E + 05 | 1.15E + 05 | 5.50E + 05 | 1.39E + 06 |

Tables 36 and 37 show the morphological data and tables 38 and 39 show the immunohistochemical data. Tables 36 and 38 are the percent of cells identified as DC morphologically under Wright-Geimsa staining and the percent of cells that were positive for the S100 protein, respectively. Tables 37 and 39 are the total cells in culture that were DC as identified morphologically and the total cells in culture that were S100+, respectively. These total cell numbers were calculated by multiplying the percents in Table 36 and 38 by the proliferation index and starting cell numbers from Table 33. At day 0, the highest average percent of morphologically identified DC and S100+ cells was present in the PL2417 adherent cultures. These cultures remained the highest at day 7 of culture while all other cultures appeared to be comparable.

TABLE 36

Average of Percent of Cells in Culture Displaying DC Morphology.

| Day | condition | DC | non-DC |
|---|---|---|---|
| 0 | MNC PL2417 | 0.00% | 100.00% |
|   | MNC TEFLON | 0.00% | 100.00% |
|   | Non-Ad. PL2417 | 1.33% | 98.67% |
|   | Adherent PL2417 | 3.00% | 97.00% |
| 7 | MNC PL2417 | 20.67% | 79.33% |
|   | MNC TEFLON | 20.33% | 79.67% |
|   | Non-Ad. PL2417 | 25.50% | 74.50% |
|   | Adherent | 50.67% | 49.33% |

TABLE 37

Average of Total Number of Cells in Culture Displaying DC Morphology.

| Day | condition | DC | non-DC |
|---|---|---|---|
| 0 | MNC PL2417 | 0.00E + 00 | 9.94E + 06 |
|   | MNC TEFLON | 0.00E + 00 | 1.49E + 07 |
|   | Non-Ad PL2417 | 1.97E + 05 | 9.73E + 06 |
|   | Adherent PL2417 | 1.59E + 04 | 2.32E + 06 |
| 7 | MNC PL2417 | 1.57E + 06 | 6.05E + 06 |
|   | MNC TEFLON | 2.16E + 06 | 8.57E + 06 |
|   | Non-Ad. PL2417 | 3.05E + 06 | 7.20E + 06 |
|   | Adherent P12417 | 2.25E + 06 | 2.18E + 06 |

TABLE 38

Average of Percent of Cells in Culture Positive for the S100 Protein.

| Day | condition | S100 neg | S100 pos |
|---|---|---|---|
| 0 | MNC PL2417 | 97.33% | 2.67% |
|   | MNC TEFLON | 97.33% | 2.67% |
|   | Non-Ad. PL2417 | 97.67% | 2.33% |
|   | Adherent PL2417 | 91.67% | 8.33% |
| 7 | MNC PL2417 | 83.67% | 18.33% |
|   | MNC TEFLON | 83.00% | 17.67% |
|   | Non-Ad. PL2417 | 86.00% | 14.00% |
|   | Adherent PL2417 | 40.67% | 64.33% |

TABLE 39

Average of Total Number of Cells in Culture Postive for the S100 Protein.

| Day | condition | S100 neg | S100 pos |
|---|---|---|---|
| 0 | MNC PL2417 | 9.68E + 06 | 2.63E + 05 |
|   | MNC TEFLON | 1.45E + 07 | 3.95E + 05 |
|   | Non.Ad. PL2417 | 9.58E + 06 | 3.45E + 05 |
|   | Adherent PL2417 | 2.29EW + 06 | 4.42E + 05 |
| 7 | MNC PL2417 | 6.35E + 06 | 1.27E + 06 |
|   | MNC TEFLON | 8.92E + 06 | 1.81E + 06 |
|   | Non-Ad. PL2417 | 8.84E + 06 | 1.41E + 06 |
|   | Adherent PL2417 | 1.61E + 06 | 3.08E + 06 |

The functional data from an allogeneic MLR demonstrated that the PL2417 adherent culture at day 7, induced equivalent T cell proliferation when compared to other cultures. However, due to the limited number of cells obtained in one experiment (Table 40), the total number of cells from the PL2417 adherent culture used in the assay was 10 fold less than the cells obtained from other cultures. In another experiment where all MLR conditions were equal (Table 41), cells from the PL2417 adherent cultures had equivalent performance as cells from other cultures. In both experiments, when used at the lower limit (1000 cells), the PL2417 adherent cells resulted in the greatest amount of T cell proliferation compared to cells cultured in the other conditions.

TABLE 40

Average T Cell Proliferation at Day 7, (counts/minute)

| condition | T cells | T + 100K | T + 10K | T + 1K | T + 100 |
|---|---|---|---|---|---|
| MNC PL2417 | 9053.0 | 52832.7 | 23047.6 | 16895.9 | nd |
| MNC TEFLON | 10006.1 | 52629.1 | 47197.4 | 17999.8 | nd |
| Non-Ad. PL2417 | 6783.6 | 47785.1 | 36405.8 | 20549.4 | nd |
| Adherent PL2417 | 6820.8 | nd | 53180.1 | 36933.4 | 11579.7 |

TABLE 41

Average T Cell Proliferation at Day 7, (counts/minute)

| condition | T cells | T + 100K | T + 10K | T + 1K |
|---|---|---|---|---|
| MNC PL2417 | 5175.2 | 560099.3 | 55822.8 | 14120.4 |
| MNC TEFLON | 6435.9 | 51846.6 | 59659.1 | 15750.1 |
| Non-Ad. PL2417 | 5875.5 | 90714.1 | 42810.9 | 8912.1 |
| Adherent PL2417 | 8495.2 | 41339.0 | 55532.5 | 21019.7 |

We performed one experiment for the purpose of comparing the ability to isolate adherent cells using a PL2417 container to the ability of using a Teflon® cell culture bag then subsequently culturing the cells in their respective containers with serum-free media plus cytokines. Non-adherent cells from both containers were also compared as were bulk PBMNC. Our results showed that the Teflon® cell culture bag yielded 3.3 fold fewer cells than the PL2417 container ($1.6 \times 10^5$ vs. $5.3 \times 10^5$). The low number of cells obtained with the Teflon® cell culture bag made proper analysis difficult.

Conclusion:

The data showed that culture of PL2417 adherent PBMNC with GM-CSF and IL-4 over a 7 day culture period resulted in a more pure population of DC. These cultures possessed the highest percent of CD1a+, CD80+, and CD86+ cells at day 7 when compared to bulk PBMNC cultures in PL2417 containers and Teflon® cell culture bags as well to the non-adherent PBMNC cultures. Morphology and immunohistochemical results indicated that PL2417 adherent cell cultures exhibited the highest percent of morphologically identified DC and S100+ cells. Furthermore, functional data from an allogeneic MLR suggested that the DC derived from the PL2417 adherent cells were more potent inducers of T cell proliferation. Thus, it was shown that PL2417 gas-permeable containers can be used to isolate adherent cells, and that culture of these cells in a serum-free, closed system environment results in a more pure population of DC.

EXAMPLE 7

Cytokine-free Culture of Dendritic Cells

Whole blood from healthy human donors was obtained and mononuclear cell preparations were made as described above in Example 1. Equipment, materials and methods were as described above. Sources for additional materials were:

Cyclic Adenosine Monophosphate (cAMP), Sigma, Cat. No. A-6885
Dibutyryl cAMP, Sigma, Cat. No. D-0627
Sodium Fluoride (NaF), Sigma, Cat. No. S-1504
Theophylline, Sigma, Cat. No. T-1633
Prostaglandin E1, Sigma, Cat. No. P-8908
Vitamin D3, Sigma, Cat. No. C-9756
Vitamin E, Sigma, Cat. No. T-3251
All Trans Retinoic Acid (Ret. A), Sigma, Cat. No. R-2625
Phorbol Myristate Acetate (PMA), Sigma, Cat. No. P-8139
Linoleic Acid-Albumin, Sigma, Cat. No. L-8384
$Ca^{++}$ Ionophore (A23187), Sigma, Cat. No. C-9275

Enrichment and Culture of Adherent Cells Using Polystyrene Tissue Culture Plates: PBMNC were resuspended in culture media (X-VIVO 15™+10% autologous serum) at $2 \times 10^6$ cells/ml. Cells were placed into 48 well polystyrene tissue culture plates (2 ml per well) and incubated for 2 hours in a 5% $CO_2$, ambient $O_2$, 37° C. humidified incubator. Non-adherent cells were removed from the plates then wells were rinsed with X-VIVO 15™ containing no serum. Cells remaining in the wells were adherent cells. These cells were cultured by adding 2 ml of X-VIVO 15™ to each well plus GM-CSF and IL-4 at final concentrations of 50 ng/ml and 1000 U/ml or the following: cAMP at 0.5 mM, dibutyryl cAMP at 0.1 mM, NaF at 0.25 mM, theophylline at 0.5 mM, PGE at 0.1 mM, Vitamin D3 at 2.5 uM, Vitamin E at 0.1%, Retinoic Acid at $10^{-6}$ M, PMA at 1 pM, Linoleic Acid at 5 ug/ml, or $Ca^{++}$ Ionophore at 10 mM. Furthermore, cells were also cultured with the above non-cytokine additives plus GM-CSF at 50 ng/ml. Cells were cultured in a 5% $CO_2$, ambient $O_2$, 37° C. humidified incubator for 7 days.

Culture of Bulk PBMNC: PBMNC cells were cultured in X-VIVO 15™ supplemented with 2 mM L-glutamine. Cultures were initiated at $5 \times 10^5$ cells/ml in PL2417 gas-permeable containers (20 ml). GM-CSF and IL-4 were added to the cultures at final concentrations of 50 ng/ml and 1000 U/ml or non-cytokine additives such as Vitamin D3 at 2.5 uM, Vitamin E at 0.1%, Linoleic Acid at 5 ug/ml, or Ca++ Ionophore at 10 mM. Addition and subtraction of cells, media, and growth factors to and from PL2417 gas-permeable containers was accomplished by spiking a Sampling Site Coupler into the sample port of the container followed by use of syringes and needles. Cells were cultured in a 5% $CO_2$, ambient $O_2$, 37° C. humidified incubator for 7 days.

Cultured cells were phenotyped as described in Example 1 above for the following markers:
PE conjugated
Isotype IgG
CD1a
CD14
CD8
CD86

Cytospin slide preparation, Wright-Geimsa and immunohistochemical staining of the cultured cells were conducted as described in Example 1 and 2 above. Mixed lymphocyte reactions (MLR's) were setup using T cells (responders) and dendritic cell enriched cultures (stimulators) from bulk PBMNC cultures, as described above in Example 1.

Results: In the set of experiments using plastic adherent cells grown in polystyrene tissue culture plates, a Day 0 analysis of the cells was not performed. However, these cultures were analyzed for the presence of DC on days 4 and 7. Analysis perfomed were cell counts, viability via propidium iodide, morphology under Wright-Geimsa staining, and immunohistochemical staining using an anti-S100 antibody. At day 4 of culture, all cultures exhibited viabilities that averaged under 80% (n=2) except for the GM-CSF/IL-4 wells (96.55%) (Table 42). The percentage of S100+ cells was also the highest in the GM-CSF/IL-4 wells (26%) while Vitamin E, Linoleic Acid and $Ca^{++}$ Ionophore containing wells possessed 19%, 20%, and 17% S100+ cells, respectively. The percentage of morphologically identified DC cells was again highest in the GM-CSF/IL-4 containing wells (8%) while all other conditions contained less than 40% DC.

TABLE 42

Day 4 Results Without GM-CSF.

| DAY | SAMPLE | TOTAL CELLS | % VIABLE | % S100 + | % DC |
|---|---|---|---|---|---|
| 4 | cAMP | 1.86E + 05 | 76.37% | 10.50% | 0.00% |
|   | dibutyryl cAMP | 2.18E + 05 | 71.00% | 6.00% | 0.00% |
|   | NaF | 2.19E + 05 | 72.46% | 0.00% | 0.00% |
|   | Theophylline | 2.12E + 05 | 75.27% | 6.00% | 0.50% |
|   | PGE | 2.54E + 05 | 71.62% | 0.00% | 3.00% |
|   | Vit D3 | 2.37E + 05 | 76.06% | 5.50% | 1.50% |
|   | Ret Acid | 1.48E + 05 | 60.67% | 7.00% | 10.00% |
|   | Vit E | 1.64E + 05 | 78.65% | 19.00% | 2.50% |
|   | PMA | 1.64E + 05 | 77.17% | 4.00% | 1.00% |
|   | Linoleic Acid | 1.99E + 05 | 78.84% | 20.00% | 3.00% |
|   | Ca ++ Iono | 1.69E + 05 | 74.04% | 17.00% | 2.50% |
|   | GM/IL4 | 2.54E + 05 | 96.55% | 26.00% | 8.00% |

When GM-CSF was added to cells containing non-cytokine additives, the percent viable cells was higher than the non-cytokine alone cultures at day 4 (Table 43). Furthermore, the percentage of S100+ cells was higher in more non-cytokine additive conditions when GM-CSF was added with the highest in the GM-CSF/cAMP wells (41%). The percent of morphologically identified DC was also enhanced when GM-CSF is added. The wells with the highest percent DC were ones with GM-CSF/IL-4, GM-CSF/Linoleic Acid and GM-CSF/Ca$^{30}$ $^+$ Ionophore.

TABLE 43

Day 4 Results With GM-CSF Present.

| DAY | SAMPLE | TOTAL CELLS | % VIABLE | % S100+ | % DC |
|---|---|---|---|---|---|
| 4 | cAMP | 2.02E + 05 | 87.60% | 41.00% | 3.00% |
|   | dibutyryl cAMP | 1.74E + 05 | 85.86% | 17.00% | 2.50% |
|   | NaF | 1.90E + 05 | 67.04% | 7.00% | 0.00% |
|   | Theophylline | 1.34E + 05 | 88.75% | 8.50% | 6.50% |
|   | PGE | 2.35E + 05 | 92.40% | 6.00% | 5.00% |
|   | Vit D3 | 1.95E + 05 | 95.86% | 8.00% | 3.00% |
|   | Ret Acid | 1.21E + 05 | 95.30% | 9.00% | 1.50% |
|   | Vit E | 1.38E + 05 | 97.48% | 26.00% | 4.50% |
|   | PMA | 1.45E + 05 | 97.60% | 20.00% | 4.50% |
|   | Linoleic Acid | 1.41E + 05 | 96.07% | 12.00% | 8.00% |
|   | Ca + + Iono | 1.66E + 05 | 96.23% | 20.00% | 9.50% |
|   | GM/IL4 | 2.36E + 05 | 97.01% | 30.00% | 11.00% |

At day 7 (Table 44), the GM-CSF/IL-4 wells contained the highest percentage of S100+ cells (46%) and morphologically identified DC (9.5%). The Linoleic Acid and Ca$^{++}$ Ionophore conditions possessed the next highest percentages of S100+ cells and morphologically identified DC.

TABLE 44

Day 7 Results Without GM-CSF.

| DAY | SAMPLE | TOTAL CELLS | % VIABLE | % S100+ | % DC |
|---|---|---|---|---|---|
| 7 | cAMP | 2.08E + 05 | 19.89% | 10.00% | 0.50% |
|   | dibutyryl CAMP | 2.59E + 05 | 58.87% | 8.00% | 0.00% |
|   | NaF | 2.18E + 05 | 44.31% | 2.50% | 0.00% |
|   | Theophylline | 1.81E + 05 | 56.49% | 7.50% | 0.00% |
|   | PGE | 2.91E + 05 | 59.78% | 5.00% | 0.00% |
|   | Vit D3 | 1.82E + 05 | 75.13% | 16.00% | 0.50% |
|   | Ret Acid | 1.66E + 05 | 45.17% | 7.00% | 0.00% |
|   | Vit E | 1.75E + 05 | 71.91% | 11.00% | 3.00% |
|   | PMA | 1.51E + 05 | 82.20% | 6.50% | 1.00% |
|   | Linoleic Acid | 1.19E + 05 | 82.69% | 25.00% | 6.00% |
|   | Ca + + Iono | 1.54E + 05 | 84.02% | 29.00% | 6.00% |
|   | GM/IL4 | 2.24E + 05 | 85.00% | 46.00% | 9.50% |

When GM-CSF was added to the wells at initiation of the cultures, this enhanced the average viabilities when compared to wells containing non-cytokine additives alone (Table 45). More wells containing the non-cytokine additives plus GM-CSF possessed higher percentages of S100+ cells and the percent of morphologically identified DC was also higher when GM-CSF was added. Addition of either cAMP, Vitamin D3, or IL-4 to GM-CSF resulted in the greatest percentages of S100+ cells.

The S100 protein is a nerve cell protein that has been associated with dendritic cells. In Table 47, at day 7 of culture, the highest percent of S100+ cells was present in the GM-CSF/IL-4 culture (13%). The $Ca^{++}$ Ionophore, Vitamin E, and Linoleic Acid cultures contained equivalent average percentages of S100+ cells while Vitamin D3 contained the lowest average percent. The table also shows the average total number of cells projected in culture positive for the S100 protein.

TABLE 45

Day 7 Results with GM-CSF Present.

| DAY | SAMPLE | TOTAL CELLS | % VIABLE | % S100+ | % DC |
|---|---|---|---|---|---|
| 7 | cAMP | 1.56E + 05 | 60.51% | 47.00% | 0.00% |
|  | dibutyryl CAMP | 1.37E + 05 | 61.25% | 14.00% | 2.50% |
|  | NaF | 1.44E + 05 | 30.61% | 5.00% | 0.00% |
|  | Theophylline | 9.65E + 05 | 59.55% | 11.00% | 3.50% |
|  | PGE | 1.84E + 05 | 60.29% | 26.50% | 5.50% |
|  | Vit D3 | 1.64E + 05 | 67.44% | 39.00% | 5.00% |
|  | Ret Acid | 1.09E + 05 | 88.52% | 14.00% | 4.00% |
|  | Vit E | 1.05E + 05 | 94.21% | 19.00% | 6.00% |
|  | PMA | 1.04E + 05 | 95.15% | 26.50% | 0.00% |
|  | Linoleic Acid | 7.85E + 05 | 82.63% | 26.00% | 9.00% |
|  | Ca ++ Iono | 1.05E + 05 | 82.69% | 26.50% | 4.50% |
|  | GM/IL4 | 2.08E + 05 | 90.66% | 48.50% | 13.00% |

The next set of experiments evaluated only 4 of the non-cytokine additives. These 4 were determined to have the highest ability to induce DC generation from PBMNC. The 4 non-cytokine additives examined were Vitamin D3, Vitamin E, $Ca^{++}$ Ionophore, and Linoleic Acid. These additives were compared to GM-CSF/IL-4. Bulk PBMNC were initiated at $5 \times 10^5$ cells/ml in X-VIVO 15™ using PL2417 gas-permeable containers (20 ml per container). As shown in Table 46, the average day 0 viability was over 99%(n=2) and by day 7, the average was over 82%.

TABLE 46

Concentration, Viability, and Total Cells in Culture.

| DAY | CONDITION | CELLS/ML | VIABILITY | TOTAL CELLS |
|---|---|---|---|---|
| 0 | All | 5.00E + 05 | 99.30% | 9.93E + 06 |
| 7 | GMCSF/IL4 | 2.40E + 06 | 90.30% | 9.50E + 06 |
|  | Ca ++ Iono | 2.22E + 06 | 83.72% | 8.29E + 06 |
|  | VIT D3 | 2.11E + 06 | 84.51% | 8.04E + 06 |
|  | VIT E | 1.87E + 06 | 82.41% | 7.52E + 06 |
|  | Linoleio Acid | 235E + 06 | 87.77% | 9.18E + 06 |

TABLE 47

S100+ Cells in Culture.

| DAY | CONDITION | % S100+ | TOTAL # OF S100+ |
|---|---|---|---|
| 0 | All | 3.5% | 3.48E + 05 |
| 7 | GMCSF/IL4 | 13.00% | 1.23E + 06 |
|  | Ca ++ Iono | 7.50% | 6.17E + 05 |
|  | VIT D3 | 5.00% | 4.16E + 05 |
|  | VIT E | 8.00% | 6.01E + 05 |
|  | Linoleio Acid | 8.50% | 7.75E + 05 |

The average percent of cells identified as DC by morphology (Table 48) at day 7 was again highest in the GM-CSF/IL-4 cultures (23%) while the non-cytokine containing cultures possessed approximately a 3–5 fold lower percentage of DC. There did not appear to be any significant differences between the 4 non-cytokine additives. When these numbers are translated into average total number of cells projected in culture displaying DC morphology (Table 48), the highest number of morphologically identified DC was present in the GM-CSF/IL-4 cultures. The $Ca^{++}$ Ionophore, Vitamin D3, and Linoleic Acid cultures possessed approximately 4 fold fewer DC. The Vitamin E culture averaged the lowest total number of morphologically identified DC.

TABLE 48

Morphologically Identified Dendritic Cells in Culture.

| DAY | CONDITION | % DC | TOTAL # OF DC |
|---|---|---|---|
| 0 | All | 0.00% | 0.00E+00 |
| 7 | GMCSF/IL4 | 23.00% | 2.18E+06 |
|   | Ca++ Iono | 7.00% | 5.74E+05 |
|   | VIT D3 | 6.50% | 5.12E+05 |
|   | VIT E | 4.00% | 2.82E+05 |
|   | Linoleic Acid | 5.00% | 4.63E+05 |

With regard to phenotype, day 0 cells showed averages of 3.7% CD1a, 11.3% CD14, 0.6% CD80 and 9.3% CD86 expression (Table 49). By day 7, these averages dropped (except for CD80) below what is normally expected in the GM-CSF/IL-4 cultures, although the highest percentage of CD1a, CD80, and CD86 expression was seen in these cultures when compared to the non-cytokine containing cultures.

TABLE 49

Percent of Phenotype in Culture.

| DAY | CONDITION | CD1a-PE | CD14-PE | CD80-PE | CD86-PE |
|---|---|---|---|---|---|
| 0 | All | 3.66% | 11.27% | 0.58% | 9.28% |
| 7 | GMSCF/IL4 | 0.78% | 0.14% | 3.47% | 3.49% |
|   | Ca ++ Iono | 0.04% | 0.26% | 2.21% | 2.32% |
|   | VIT D3 | 0.10% | 0.53% | 2.65% | 2.62% |
|   | VIT E | 0.08% | 0.73% | 1.97% | 2.75% |
|   | Linoleic Add | 0.08% | 0.46% | 2.61% | 2.72% |

The functional capacity of cultured cells to induce T cell proliferation was measured in an allogeneic MLR. Table 50 shows the amount of proliferation as an increase over background proliferation (T cells alone). Data from day 7 suggest that cells from the non- cytokine additive cultures appear to induce T cell proliferation to a capacity approaching that of the GM-CSF/IL-4 cultured cells, especially at the cell culture:T cell ratio of 1:1. At the greatest ratio of 1:100, the differences in capacity to induce T cell proliferation is marginal between the GM-CSF/IL-4 cultured cells and the non-cytofine additive cultured cells.

TABLE 50

Allogeneic MLR. Increase Over Background Proliferation at Cell Culture:T cell Ratios.

| DAY | CONDITION | 1:1 | 1:10 | 1:100 |
|---|---|---|---|---|
| 7 | GMCSF/IL4 | 7.5 | 4.8 | 1.8 |
|   | Ca++ Iono | 4.8 | 1.8 | 0.9 |
|   | VIT D3 | 6.9 | 2.7 | 1.4 |
|   | VIT E | 6.3 | 2.6 | 1.7 |
|   | Linoleic Acid | 6.1 | 3.1 | 1.1 |

Conclusion:

It is possible to culture-derive dendritic cells in clinically useful numbers without the use of cytokines, although the dendritic cell numbers will generally be lower than those achieved using GM-CSF and IL-4. In place of cytokines, agents such as $Ca^{++}$ ionophore, Vitamin D3, Vitamin E, and linoleic acid show the most promise.

The present invention has been described above for illustration and understanding. Given the teachings herein, it will be readily apparent to one of ordinary skill in the art of hematopoietic cell culture that certain changes and modifications may be made without departing from the spirit or scope of the appended claims.

What is claimed is:

1. A method for producing a culture enriched for human dendritic cells for therapeutic purposes, said method comprising:
    (a) providing mononuclear cells from peripheral or umbilical cord blood or bone marrow of an individual human donor, wherein said mononuclear cells comprise dendritic cell precursors,
    (b) culturing said mononuclear cells in a culture container in a culture medium that supports mononuclear cell culture, said medium further containing an effective amount of an additive that differentiates dendritic cell precursors into dendritic cells, wherein said additive is prostaglandin E, and
    (c) maintaining the culture of said mononuclear cells to produce a culture enriched for dendritic cells as evidenced by at least about 2.5% of total cells in the culture exhibiting dendritic cell processes.

2. A method for producing a culture enriched for human dendritic cells for therapeutic purposes, said method comprising:
    (a) providing mononuclear cells from peripheral or umbilical cord blood or bone marrow of an individual human donor, wherein said mononuclear cells comprise dendritic cell precursors,
    (b) culturing said mononuclear cells in a culture container in a culture medium that supports mononuclear cell culture, said medium further containing an effective amount of an additive that differentiates dendritic cell precursors into dendritic cells, wherein said additive is vitamin E, and
    (c) maintaining the culture of said mononuclear cells to produce a culture enriched for dendritic cells as evidenced by at least about 2.5% of total cells in the culture exhibiting dendritic cell processes.

3. A method for producing a culture enriched for human 'dendritic cells for therapeutic purposes, said method comprising:
    (a) providing mononuclear cells from peripheral or umbilical cord blood or bone marrow of an individual human donor, wherein said mononuclear cells comprise dendritic cell precursors,
    (b) culturing said mononuclear cells in a culture container in a culture medium that supports mononuclear cell culture, said medium further containing an effective amount of an additive that differentiates dendritic cell precursors into dendritic cells, wherein said additive is retinoic acid, and
    (c) maintaining the culture of said mononuclear cells to produce a culture enriched for dendritic cells as evidenced by at least about 2.5% of total cells in the culture exhibiting dendritic cell processes.

4. A method for producing a culture enriched for human dendritic cells for therapeutic purposes, said method comprising:
    (a) providing mononuclear cells from peripheral or umbilical cord blood or bone marrow of an individual human donor, wherein said mononuclear cells comprise dendritic cell precursors,
    (b) culturing said mononuclear cells in a culture container in a culture medium that supports mononuclear cell culture, said medium further containing an effective amount of an additive that differentiates dendritic cell precursors into dendritic cells, wherein said additive is a fatty acid selected from the group consisting of linoleic acid, palmitic acid, stearic acid, palmitoleic acid, oleic acid and linolenic acid, and (c) maintaining the culture of said mononuclear cells to produce a culture enriched for dendritic cells as evidenced by at least about 2.5% of total cells in the culture exhibiting dendritic cell processes.

5. The method of claim 4, wherein said additive is linoleic acid.

6. A method for producing a culture enriched for human dendritic cells for therapeutic purposes, said method comprising:

(a) providing mononuclear cells from peripheral or umbilical cord blood or bone marrow of an individual human donor, wherein said mononuclear cells comprise dendritic cell precursors, (b) incubating said mononuclear cells in a culture container for a time sufficient to allow a subset of cells to adhere to the inner surface of said culture container, after which the cells which do not adhere to the inner surface are removed, (c) culturing said mononuclear cells in a culture container in a culture medium that supports mononuclear cell culture, said medium further containing an effective amount of an additive that differentiates dendritic cell precursors into dendritic cells, wherein said additive is calcium ionophore, and (d) maintaining the culture of said mononuclear cells to produce a culture enriched for dendritic cells as evidenced by at least about 2.5%of total cells in the culture exhibiting dendritic cell processes.

7. The method of claim 6, wherein said calcium ionophore is A23187.

8. The method of any of claims 1–4 or 6, wherein said medium further comprises granulocyte-macrophage colony-stimulating factor(GM-CSF).

9. The method of claim 8, wherein said medium further comprises interleukin-4 (IL-4).

10. A method for producing a culture enriched for human dendritic cells for therapeutic purposes, said method comprising:

(a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing GM-CSF and an effective amount of an additive that differentiates dendritic cell precursors into dendritic cells, wherein said additive is theophylline, and (c) maintaining the culture of said mononuclear cells to produce a culture enriched for dendritic cells as evidenced by at least about 2.5% of total cells in the culture exhibiting dendritic cell processes.

11. A method for producing a culture enriched for human dendritic cells for therapeutic purposes, said method comprising:

(a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing GM-CSF and an effective amount of an additive that differentiates dendritic cell precursors into dendritic cells, wherein said additive is dibutyryl cyclic AMP, and (c) maintaining the culture of said mononuclear cells to produce a culture enriched for dendritic cells as evidenced by at least about 2.5% of total cells in the culture exhibiting dendritic cell processes.

12. A method for producing a culture enriched for human dendritic cells for therapeutic purposes, said method comprising:

(a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing GM-CSF and an effective amount of an additive that differentiates dendritic cell precursors into dendritic cells, wherein said additive is Vitamin D3, and (c) maintaining the culture of said mononuclear cells to produce a culture enriched for dendritic cells as evidenced by at least about 2.5% of total cells in the culture exhibiting dendritic cell processes.

13. The method of any of claims 10–12, wherein said medium further comprises IL-4.

14. The method of any of claims 1–4 or 10–12, wherein, prior to said culturing step (b), the mononuclear cells are incubated in said culture container for a time sufficient to allow a subset of cells to adhere to the inner surface of said culture container, after which the cells which do not adhere to the inner surface are removed.

15. The method of any of claims 1–4, 6 or 10–12, wherein said mononuclear cells comprise pre-selected CD34+ cells.

16. The method of any of claims 1–4, 6 or 10–12 further comprising, prior to said culturing step, depleting said mononuclear cells of T-cells.

17. The method of any of claims 1–4, or 10–12 further comprising, during said culturing step or maintaining step, contacting said dendritic cells with an antigen to produce antigen-pulsed dendritic cells.

18. The method of claim 17 wherein said antigen is selected from the group consisting of tumor antigens, viral antigens, bacterial antigens, and cell surface antigens.

19. A method for producing antigen-specific human T-cells for therapeutic use, said method comprising:

(a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing an effective amount of an additive that differentiates dendritic cell precursors into dendritic cells, wherein said additive is prostaglandin E, (c) maintaining the culture of said mononuclear cells to produce a culture enriched for dendritic cells as evidenced by at least about 2.5% of total cells in the culture exhibiting dendritic cell processes, (d) pulsing said dendritic cells with an antigen to produce antigen-pulsed dendritic cells, (e) providing T-cells from an individual human donor, and (f) co-culturing at least a portion of said antigen-pulsed dendritic cells and said T-cells to produce antigen-specific T-cells.

20. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors,
   (b) culturing said mononuclear cells in a culture container in a culture medium that supports mononuclear cell culture, said medium further containing an effective amount of an additive that differentiates dendritic cell precursors into dendritic cells, wherein said additive is Vitamin E,
   (c) maintaining the culture of said mononuclear cells to produce a culture enriched for dendritic cells as evidenced by at least about 2.5% of total cells in the culture exhibiting dendritic cell processes
   (d) pulsing said dendritic cells with an antigen to produce antigen-pulsed dendritic cells,
   (e) providing T-cells from an individual human donor, and
   (f) co-culturing at least a portion of said antigen-pulsed dendritic cells and said T-cells to produce antigen-specific T-cells.

21. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors,
   (b) culturing said mononuclear cells in a culture container in a culture medium that supports mononuclear cell culture, said medium further containing an effective amount of an additive that differentiates dendritic cell precursors into dendritic cells, wherein said additive is retinoic acid,
   (c) maintaining the culture of said mononuclear cells to produce a culture enriched for dendritic cells as evidenced by at least about 2.5% of total cells in the culture exhibiting dendritic cell processes,
   (d) pulsing said dendritic cells with an antigen to produce antigen-pulsed dendritic cells,
   (e) providing T-cells from an individual human donor, and
   (f) co-culturing at least a portion of said antigen-pulsed dendritic cells and said T-cells to produce antigen-specific T-cells.

22. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors,
   (b) culturing said mononuclear cells in a culture container in a culture medium that supports mononuclear cell culture, said medium further containing an effective amount of an additive that differentiates dendritic cell precursors into dendritic cells, wherein said additive is a fatty acid selected from the group consisting of linoleic acid, palmitic acid, stearic acid, palmitoleic acid, oleic acid and linolenic acid, and
   (c) maintaining the culture of said mononuclear cells to produce a culture enriched for dendritic cells as evidenced by at least about 2.5% of total cells in the culture exhibiting dendritic cell processes,
   (d) pulsing said dendritic cells with an antigen to produce antigen-pulsed dendritic cells,
   (e) providing T-cells from an individual human donor, and
   (f) co-culturing at least a portion of said antigen-pulsed dendritic cells and said T-cells to produce antigen-specific T-cells.

23. The method of claim 22, wherein said additive is linoleic acid.

24. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors,
   (b) incubating said mononuclear cells in a culture container for a time sufficient to allow a subset of cells to adhere to the inner surface of said culture container, after which the cells which do not adhere to the inner surface are removed,
   (c) culturing said mononuclear cells in a culture container in a culture medium that supports mononuclear cell culture, said medium further containing an effective amount of an additive that differentiates dendritic cell precursors into dendritic cells, wherein said additive is calcium ionophore, and
   (d) maintaining the culture of said mononuclear cells to produce a culture enriched for dendritic cells as evidenced by at least about 2.5% of total cells in the culture exhibiting dendritic cell processes
   (e) pulsing said dendritic cells with an antigen to produce antigen-pulsed dendritic cells,
   (f) providing T-cells from an individual human donor, and
   (g) co-culturing at least a portion of said antigen-pulsed dendritic cells and said T-cells to produce antigen-specific T-cells.

25. The method of claim 24, wherein said calcium ionophore is A23187.

26. The method of any of claims 19–22 or 24, wherein said medium further comprises GM-CSF.

27. The method of claim 26, wherein said medium further comprises IL-4.

28. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors,
   (b) culturing said mononuclear cells in a culture container in a culture medium that supports mononuclear cell culture, said medium further containing GM-CSF and an effective amount of an additive that differentiates dendritic cell precursors into dendritic cells, wherein said additive is theophylline, and
   (c) maintaining the culture of said mononuclear cells to produce a culture enriched for dendritic cells as evidenced by at least about 2.5% of total cells in the culture exhibiting dendritic cell processes,
   (d) pulsing said dendritic cells with an antigen to produce antigen-pulsed dendritic cells,
   (e) providing T-cells from an individual human donor, and
   (f) co-culturing at least a portion of said antigen-pulsed dendritic cells and said T-cells to produce antigen-specific T-cells.

29. A method for producing antigen-specific human T-cells for therapeutic use, said method comprising:
   (a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing GM-CSF and an effective amount of an additive that differentiates dendritic cell precursors into dendritic cells, wherein said additive is dibutyryl cyclic AMP, and (c) maintaining the culture of said mononuclear cells to produce a culture enriched for dendritic cells as evidenced by at least about 2.5% of total cells in the culture exhibiting dendritic cell processes, (d) pulsing said dendritic cells with an antigen to produce antigen-pulsed dendritic cells, (e) providing T-cells from an individual human donor, and (f) co-culturing at least a portion of said antigen-pulsed dendritic cells and said T-cells to produce antigen-specific T-cells.

30. A method for producing antigen-specific human T-cells for therapeutic use, said method comprising:

(a) providing mononuclear cells from peripheral or umbilical cord blood or bone marrow of an individual human donor, wherein said mononuclear cells comprise dendritic cell precursors, (b) culturing said mononuclear cells in a culture container in a culture medium that supports mononuclear cell culture, said medium further containing GM-CSF and an effective amount of an additive that differentiates dendritic cell precursors into dendritic cells, wherein said additive is Vitamin D3, and (c) maintaining the culture of said mononuclear cells to produce a culture enriched for dendritic cells as evidenced by at least about 2.5% of total cells in the culture exhibiting dendritic cell processes, (d) pulsing said dendritic cells with an antigen to produce antigen-pulsed dendritic cells, (e) providing T-cells from an individual human donor, and (f) co-culturing at least a portion of said antigen-pulsed dendritic cells and said T-cells to produce antigen-specific T-cells.

31. The method of any of claims 28–30, wherein said medium further comprises IL-4.

32. The method of any of claims 19–22, 24 or 28–30 wherein, prior to said culturing step (b), the mononuclear cells are incubated in said culture container for a time sufficient to allow a subset of cells to adhere to the inner surface of said culture container, after which the cells which do not adhere to the inner surface are removed.

33. The method of any of claims 19–22, 24 or 28–30, wherein said mononuclear cells comprise pre-selected CD34+ cells.

34. The method of any of claims 19–22, 24 or 28–30 wherein the provided T-cells are either culture-derived or pre-selected for expression of antigens selected from the group consisting of CD8, CD4, and CD45RO.

35. The method of any of claims 19–22, 24 or 28–30 wherein said T-cells and said mononuclear cells are donated either by the same individual or by two different, HLA-matched individuals.

36. The method of any of claims 19–22, 24 or 28–30 wherein said antigen is selected from the group consisting of tumor antigens, viral antigens, bacterial antigens, and cell surface antigens.

* * * * *